United States Patent
Forsberg et al.

(10) Patent No.: US 12,209,131 B2
(45) Date of Patent: Jan. 28, 2025

(54) ANTI-IL1RAP ANTIBODY COMPOSITIONS

(71) Applicant: Cantargia AB, Lund (SE)

(72) Inventors: Göran Forsberg, Eslöv (SE); David Liberg, Lomma (SE); Kjell Sjöström, Lund (SE); Karin von Wachenfeldt, Lund (SE)

(73) Assignee: Cantargia AB, Lund (SE)

( * ) Notice: Subject to any disclaimer, the term of this patent is extended or adjusted under 35 U.S.C. 154(b) by 846 days.

(21) Appl. No.: 17/267,157

(22) PCT Filed: Aug. 15, 2019

(86) PCT No.: PCT/EP2019/071974
§ 371 (c)(1),
(2) Date: Feb. 9, 2021

(87) PCT Pub. No.: WO2020/035577
PCT Pub. Date: Feb. 20, 2020

(65) Prior Publication Data
US 2022/0267454 A1    Aug. 25, 2022

(30) Foreign Application Priority Data

Aug. 16, 2018  (SE) .................................. 1850983-6

(51) Int. Cl.
*C07K 16/28* (2006.01)
*A61P 35/00* (2006.01)
*C07K 16/24* (2006.01)

(52) U.S. Cl.
CPC .......... *C07K 16/2866* (2013.01); *A61P 35/00* (2018.01); *C07K 16/244* (2013.01); *C07K 2317/21* (2013.01); *C07K 2317/24* (2013.01); *C07K 2317/33* (2013.01); *C07K 2317/526* (2013.01); *C07K 2317/62* (2013.01)

(58) Field of Classification Search
None
See application file for complete search history.

(56) References Cited

U.S. PATENT DOCUMENTS

| | | | |
|---|---|---|---|
| 5,225,539 A | 7/1993 | Winter | |
| 6,180,370 B1 | 1/2001 | Queen et al. | |
| 9,403,906 B2 | 8/2016 | Fioretos et al. | |
| 9,458,237 B2 | 10/2016 | Fioretos et al. | |
| 9,796,783 B2 * | 10/2017 | Ågerstam | A61P 1/18 |
| 10,005,841 B2 | 6/2018 | Fioretos et al. | |
| 10,005,842 B2 | 6/2018 | Fioretos et al. | |
| 10,100,119 B2 * | 10/2018 | Ågerstam | A61P 31/04 |
| 10,287,357 B2 * | 5/2019 | Ågerstam | A61P 35/02 |
| 10,562,971 B2 * | 2/2020 | Ågerstam | A61P 11/06 |
| 10,752,692 B2 * | 8/2020 | Ågerstam | A61P 29/00 |
| 10,878,703 B2 | 12/2020 | Fioretos et al. | |
| 10,995,144 B2 | 5/2021 | Fioretos et al. | |
| 11,236,172 B2 * | 2/2022 | Ågerstam | A61P 35/02 |
| 11,359,025 B2 | 6/2022 | Jiang et al. | |
| 11,479,610 B2 | 10/2022 | Liberg et al. | |
| 2006/0228300 A1 | 10/2006 | Chang et al. | |
| 2006/0228357 A1 | 10/2006 | Chang et al. | |
| 2007/0086942 A1 | 4/2007 | Chang et al. | |
| 2007/0140966 A1 | 6/2007 | Chang et al. | |
| 2017/0121420 A1 | 5/2017 | Heidrich et al. | |
| 2018/0002430 A1 * | 1/2018 | Ågerstam | A61P 13/12 |
| 2018/0044425 A1 * | 2/2018 | Ågerstam | A61P 25/28 |
| 2021/0261674 A1 | 8/2021 | Fioretos et al. | |
| 2022/0106396 A1 | 4/2022 | Ågerstam et al. | |
| 2022/0267454 A1 | 8/2022 | Forsberg et al. | |

FOREIGN PATENT DOCUMENTS

| | | | | |
|---|---|---|---|---|
| JP | 2010116338 A | 5/2010 | | |
| WO | WO 93/08829 A1 | 5/1993 | | |
| WO | 9400136 A1 | 1/1994 | | |
| WO | WO 96/27011 A1 | 9/1996 | | |
| WO | WO 02/43478 A2 | 6/2002 | | |
| WO | 2011021014 | 2/2011 | | |
| WO | WO 2013/074569 A1 | 5/2013 | | |
| WO | 2015132602 | 9/2015 | | |
| WO | WO-2015132602 A1 * | 9/2015 | ........... | A61K 39/395 |
| WO | WO-2016020502 A1 * | 2/2016 | ......... | A61K 47/6803 |
| WO | 2017093448 A1 | 6/2017 | | |
| WO | 2018071910 | 4/2018 | | |
| WO | 2012098407 | 7/2020 | | |
| WO | 2022136569 | 6/2022 | | |

OTHER PUBLICATIONS

Spiess et al. Molecular Immunology. 67: 95-106; Published: Jan. 27, 2015 (Year: 2015).*
Forsberg. IL1RAP as a therapeutic target; PEGS Boston Summit Apr. 30-May 4, 2018 (Year: 2018).*
Agerstam et al.: "Antibodies targeting human IL1RAP (IL1R3) show therapeutic effects in xenograft models of acute myeloid leukemia", PNAS, vol. 112, No. 34, Aug. 25, 2015, pp. 10786-10791, XP055308490, DOI: 10.1073/pnas.1422749112.
Agerstam et al.: "IL1RAP antibodies block IL-1 induced expansion of candidate CML stem cells and mediate cell killing in xenograft models", Blood, vol. 128, No. 23, Sep. 12, 2016, pp. 2683-2693, XP055494589, Doi: 10.1182/blood-2015-11-679985.
Barbas, C. F. et al. "in vitro evolution of a neutralizing human antibody to human immunodeficiency virus type 1 to enhance affinity and broaden strain cross-reactivity", Proc. Natl. Acad. Sci. USA, vol. 91: 3809-13, Apr. 1994.
Blumberg. H., et al. IL-1RLZ and its Ligands contribute to the cytokine network in Psoriasis, J Immunol 2010, 185: 4354-62.

(Continued)

*Primary Examiner* — Juliet C Switzer
*Assistant Examiner* — Katherine Ann Holtzman
(74) *Attorney, Agent, or Firm* — McNeill PLLC

(57) ABSTRACT

The present invention relates to antibody compositions directed to Interleukin 1 Receptor Accessory Protein (IL1RAP) and their use in the treatment and diagnosis of diseases associated with IL1RAP, such as inflammatory, autoimmune, autoinflammatory and neoplastic disorders.

5 Claims, 6 Drawing Sheets
Specification includes a Sequence Listing.

(56) References Cited

OTHER PUBLICATIONS

Brennan, M. et al. "Preparation of bispecific antibodies by chemical recombination of monoclonal immunoglobulin G1 fragments", Science, Jul. 5, 1985, 229(4708): 81-3.
Dinarello, C. A. "The IL-1 family and inflammatory diseases", Clin Exp Rheumatol, Sep.-Oct. 2002, vol. 20(5 Suppl 27): S1-13.
Dinarello, C.A. "Proinflammatory cytokines", Chest. Aug. 2000; 118(2): 503-508.
Dinarello, C. et al. "Treating inflammation by blocking interleukin-1 in a broad spectrum of diseases", Aug. 2012, Nature Reviews Drug Discov, vol. 11(8), pp. 633-652.
Dinarello, Charles A. "An expanding role for interleukin-1 blockade from Gout to cancer", Dec. 2014, Mol. Med. 20(suppl. 1):S43-S58.
Dinarello, Charles A. "Biologic basis for Interleukin-1 in Disease", Blood Mar. 15, 1996, 87(6): 2095-147).
Foster, A.M., et al. "IL-36 promotes myeloid cell infiltration, activation and inflammatory activity in skin", J Immunol, Jun. 15, 2014, 192(12): 6053-61.
Gabay C. and Towne, J. E. "Regulation and function of interleukin-36 cytokines in homeostasis and pathological conditions", J Leukocyte Biol Apr. 2015, vol. 97: 645-52.
Greener et al. "In Vitro Mutagenesis Protocols", Humana press, NJ, 1996.
Gruber et al. "Efficient tumor cell lysis mediated by a bispecific single chain antibody expressed in *Escherichia coli*", J. Immunol. Jun. 1, 1994, vol. 152(11): 5368-5374.
Gudjonsson, J. et al.: "Mouse Models of Psoriasis", J Investigative Dermatology (2007) 127: 1292-1308, doi:10.1038/sj.jid.5700807.
Günther, S. et al: "Molecular determinants of Agonist and Antagonist Signaling through the IL-36 receptor", J. Immunol. 2014 193: 921-30.
Hawkins, R.E. et al. "Selection of phage antibodies by binding affinity: Mimicking affinity maturation", J. Mol. Biol. Aug. 5, 1992, vol. 226(3): 889-96.
Hollinger, P. et al. "Diabodies: Small bivalent and bispecific antibody fragments", Proc. Natl. Acad. Sci. USA, vol. 90: 6444-6448, Jul. 1993.
Huang, J. et al., "Recruitment of IRAK to the interleukin 1 receptor complex requires interleukin 1 receptor accessory protein", Proc. Natl. Acad. Sci. USA, vol. 94, Nov. 25, 1997, pp. 12829-12832.
Jackson, J. R. et al. "In vitro antibody maturation. Improvement of a high affinity, neutralizing antibody against IL-1 beta", J. Immunol. Apr. 1, 1995, 154(7): 3310-19 (1995).
Jones, P. T. et al., "Replacing the complementarity-determining regions in a human antibodywith those from a mouse"; Nature, vol. 321, May 29, 1986, 522-525.
Järås, M. et al., "Isolation and killing of candidate chronic myeloid leukemia stem cells by antibody targeting of IL-1 receptor accessory protein", PNAS, Sep. 14, 2010, vol. 107, No. 37, 16280-16285.
Kabat et al."Sequences of Proteins of Immunological Interest", 5th Ed. Public Health Service, National Institutes of Health, Bethesda, MD. (1991).
Kolkman, J. A. et al. "Directed evolution of proteins by exon shuffling", Nat Biotechnol. May 2001; 19(5):423 -8.
Kontermann, R. et al.: "Bispecific antibodies", Drug Discovery Today, vol. 20(7) Jul. 2015.
Kopsidas, G. et al. "In vitro improvement of a shark IgNAR antibody by QB replicase mutation and ribosome display mimics in vivo affinity maturation", Immunol Lett. 2006, vol. 107(2) Nov. 15, 2006:163-8.
Kostelny, S. A. et al. "Formation of a bispecific antibody by the use of leucine zippers", J. Immunol., Mar. 1, 1992, vol. 148(5): 1547-1553.
Kundu-Raychaudhuri, S. et al.: "Severe combined immunodeficiency mouse-psoriatic human skin xenograft model: A modern tool connecting bench to bedside", Indian J Dermatology, Venereology, and Leprology vol. 80(3) May-Jun. 2014: 204-213.

Labrijn, A. F. et al. "Efficient generation of stable bispecific IgG1 by controlled Fab-arm exchange", Proc Natl Acad Sci USA, Mar. 26, 2013; vol. 110(13): 5145-5150.
Liew, F. Y. et al. "Interleukin-33 in health and disease", Nat Rev Immunol Sep. 19, 2016, 16:676-89.
Lindhofer, H. et al. "Preferential species-restricted heavy-light chain pairing in rat/mouse quadromas. Implications for a single-step purification of bispecific antibodies", J Immunol. Jul. 1995, 155(1): 219-225 (1995).
Liu, X. et al.: "Structural insights into the interaction of IL-33 with its receptors", PNAS Sep. 10, 2013, vol. 110(37): 14918-23.
Lonberg, N. et al. "Antigen-specific human antibodies from mice comprising four distinct genetic modifications", Nature 368: 856-859 (1994).
Marks, J.D. et al. "By-passing immunization: building high affinity human antibodies by chain shuffling", Biotechnology, Jul. 1992, 10(7): 779-83.
Milstein, C. et al. "Hybrid hybridomas and their use in immunohistochemistry", Nature, 305: 537-540 (1983).
Mutamba, S., et al. "Expression of IL-1Rrp2 by human myelomonocytic cells is unique to DCs and facilitates DC maturation by IL-1F8 and IL-1F9", Eur J Immunol, Mar. 2012, 42(3): 607-17.
Peled, J. U. et al. "The biochemistry of somatic hypermutation", Annu Rev Immunol. 2008, 26:481-511.
Presta, Leonard G.: "Antibody engineering", Struct. Biol. , vol. 2, Issue 4, Aug. 1992, pp. 593-596. https://doi.org/10.1016/0959-440X(92)90091-K.
Queen, C. et al. "A humanized antibody that binds to the interleukin 2 receptor", PNAS USA, Dec. 1989, vol. 86: 10029-33.
Riechmann, L. et al., "Reshaping human antibodies for therapy", Nature, vol. 332, Mar. 24, 1988, 323-327.
Schier, R. et al. "Identification of functional and structural aminoacid residues by parsimonious mutagenesis", Gene, vol. 169(2): 147-155, 1996.
Schmitz, J. et al. "IL-33, an Interleukin-1-like Cytokine that signals via the IL-1 Receptor-related Protein ST2 and induces T helper type 2-associated cytokines", Immunity Nov. 2005, vol. 23, 479-90.
Shalaby, M. R. et al. "Development of humanized bispecific antibodies reactive with cytotoxic lymphocytes and tumor cells overexpressing the HER2 protooncogene", J. Exp. Med. vol. 175, Jan. 1992: 217-225.
Suresh, M. R. et al. "Bispecific monoclonal antibodies from hybrid hybridomas", Methods Enzymol. 1986, vol. 121: 210-28.
Thie, H. et al. "Therapeutic Antibodies", Methods Mol Biol, vol. 525: 309-322 (2009).
Thomas, C et al.: "Structure of the activating IL-1 receptor signaling complex", Nat Struct Mol Biol 2012 19(4):455-457.
Thompson, J. D. et al. "Clustal W: improving the sensitivity of progressive multiple sequence alignment through sequence weighting, position-specific gap penalties and weight matrix choice", Nucleic Acids Res. vol. 22(22) Nov. 11, 1994, 4673-4680.
Traunecker et al. "Bispecific single chain molecules (Janusins) target cytotoxic Lymphocytes on HIV infected cells", Embo J., vol. 10(12): 3655-3659 (1991).
Tutt, A. et al. "Trispecific F(ab' )3 derivatives that use cooperative signaling via the TCR/CD3 complex and CD2 to activate and redirect resting cytotoxic T cells", J. Immunol. Jul. 1, 1991, vol. 147(1): 60-69.
Verhoeyen, M. et al., "Reshaping Human Antibodies: Grafting an Antilysozyme Activity", Science, New Series, vol. 239, No. 4847 (Mar. 25, 1988), pp. 1534-1536.
Wang et al., "Structural insights into the assembly and activation of IL-1b with its receptors", nature immunology vol. 11 No. 10 Oct. 2010, 905-912, doi:10.1038/ni.1925.
Wu C. et al. "Molecular construction and optimization of antihuman IL-1 a/B dual variable domain immunoglobulin (DVD-lg tm) molecules", MAbs 1:4 : 339-347, Jul./Aug. 2009.
Wu C. et al. "Simultaneous targeting of multiple disease mediators by a dual-variable-domain immunoglobulin", Nat. Biotechnol. 25; 1290-1297 (2007).
Xu et al. "Production of bispecific antibodies in "knobs-into-holes" using a cell-free expression system", mAbs 7(1): 231-242; Jan./Feb. 2015.

(56) References Cited

OTHER PUBLICATIONS

Yelton, D.E. et al. "Affinity maturation of the BR96 anti-carcinoma antibody by codon-based mutagenesis", J. Immunol. Aug. 15, 1995, vol. 55(4): 1994-2004.
Yoon, et al. "Antibodies to Domains II and III of the IL-1 Receptor Accessory Protein Inhibit IL-1 B Activity but not Binding: Regulation of IL-1 responses is via type I receptor, not the accessory protein", J Immunol 1998; 160:3170-3179.

* cited by examiner

SEQUENCE LISTING

<160> NUMBER OF SEQ ID NOS: 38

<210> SEQ ID NO 1
<211> LENGTH: 108
<212> TYPE: PRT
<213> ORGANISM: Artificial Sequence
<220> FEATURE:
<223> OTHER INFORMATION: CAN04 variant 6 variable light chain (VL)

<400> SEQUENCE: 1

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Gly Ile Asn Asn Tyr
                20                  25                  30

Leu Asn Trp Tyr Gln Gln Lys Pro Gly Lys Ala Pro Lys Leu Leu Ile
            35                  40                  45

His Tyr Thr Ser Gly Leu His Ala Gly Val Pro Ser Arg Phe Ser Gly
        50                  55                  60

Ser Gly Ser Gly Thr Asp Tyr Thr Leu Thr Ile Ser Ser Leu Glu Pro
65                  70                  75                  80

Glu Asp Val Ala Thr Tyr Tyr Cys Gln Gln Tyr Ser Ile Leu Pro Trp
                85                  90                  95

Thr Phe Gly Gly Gly Thr Lys Val Glu Ile Lys Arg
            100                 105

<210> SEQ ID NO 2
<211> LENGTH: 108
<212> TYPE: PRT
<213> ORGANISM: Artificial Sequence
<220> FEATURE:
<223> OTHER INFORMATION: CAN04 variable light chain (VL) VL1

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Gly Ile Asn Asn Tyr
                20                  25                  30

Leu Asn Trp Tyr Gln Gln Lys Pro Gly Lys Ala Pro Lys Leu Leu Ile
            35                  40                  45

His Tyr Thr Ser Gly Leu His Ala Gly Val Pro Ser Arg Phe Ser Gly
        50                  55                  60

Ser Gly Ser Gly Thr Asp Tyr Thr Leu Thr Ile Ser Ser Leu Gln Pro
65                  70                  75                  80

Glu Asp Val Ala Thr Tyr Tyr Cys Gln Gln Tyr Ser Ile Leu Pro Trp
                85                  90                  95

Thr Phe Gly Gly Gly Thr Lys Val Glu Ile Lys Arg
            100                 105

```
<210> SEQ ID NO 3
<211> LENGTH: 108
<212> TYPE: PRT
<213> ORGANISM: Artificial Sequence
<220> FEATURE:
<223> OTHER INFORMATION: CAN04 variable light chain (VL) VL3

<400> SEQUENCE: 3

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Gly Ile Asn Asn Tyr
            20                  25                  30

Leu Asn Trp Tyr Gln Gln Lys Pro Gly Lys Ala Pro Lys Leu Leu Ile
        35                  40                  45

His Tyr Thr Ser Gly Leu His Ala Gly Val Pro Ser Arg Phe Ser Gly
    50                  55                  60

Ser Gly Ser Gly Thr Asp Phe Thr Leu Thr Ile Ser Ser Leu Glu Pro
65                  70                  75                  80

Glu Asp Val Ala Thr Tyr Tyr Cys Gln Gln Tyr Ser Ile Leu Pro Trp
                85                  90                  95

Thr Phe Gly Gly Gly Thr Lys Val Glu Ile Lys Arg
            100                 105

<210> SEQ ID NO 4
<211> LENGTH: 117
<212> TYPE: PRT
<213> ORGANISM: Artificial Sequence
<220> FEATURE:
<223> OTHER INFORMATION: CAN04 variant 6 variable heavy chain (VH)

<400> SEQUENCE: 4

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Thr Ser Ser
            20                  25                  30

Trp Met Asn Trp Val Arg Gln Ala Pro Gly Gln Gly Leu Glu Trp Met
        35                  40                  45

Gly Arg Ile Tyr Pro Gly Asp Gly Asn Thr His Tyr Ala Gln Lys Phe
    50                  55                  60

Gln Gly Arg Val Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Gly Glu Gly Tyr Leu Asp Pro Met Asp Tyr Trp Gly Gln Gly Thr Leu
            100                 105                 110

Val Thr Val Ser Ser
        115

<210> SEQ ID NO 5
<211> LENGTH: 117
<212> TYPE: PRT
<213> ORGANISM: Artificial Sequence
<220> FEATURE:
<223> OTHER INFORMATION: CAN04 variable heavy chain (VH) VH1

<400> SEQUENCE: 5

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Ser Ser
            20                  25                  30
```

Trp Met Asn Trp Val Arg Gln Ala Pro Gly Gln Gly Leu Glu Trp Met
            35                  40                  45

Gly Arg Ile Tyr Pro Gly Asp Gly Asn Thr His Tyr Ala Gln Lys Phe
        50                  55                  60

Gln Gly Arg Val Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Gly Glu Gly Tyr Leu Asp Pro Met Asp Tyr Trp Gly Gln Gly Thr Leu
                100                 105                 110

Val Thr Val Ser Ser
            115

<210> SEQ ID NO 6
<211> LENGTH: 117
<212> TYPE: PRT
<213> ORGANISM: Artificial Sequence
<220> FEATURE:
<223> OTHER INFORMATION: CAN04 variable heavy chain (VH) VH3

<400> SEQUENCE: 6

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Ser
            20                  25                  30

Trp Met Asn Trp Val Arg Gln Ala Pro Gly Lys Gly Leu Glu Trp Met
            35                  40                  45

Gly Arg Ile Tyr Pro Gly Asp Gly Gln Thr His Tyr Ala Gln Lys Phe
        50                  55                  60

Gln Gly Arg Val Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Gly Glu Gly Tyr Leu Asp Pro Met Asp Tyr Trp Gly Gln Gly Thr Leu
                100                 105                 110

Val Thr Val Ser Ser
            115

<210> SEQ ID NO 7
<211> LENGTH: 117
<212> TYPE: PRT
<213> ORGANISM: Artificial Sequence
<220> FEATURE:
<223> OTHER INFORMATION: CAN04 variable heavy chain (VH) VH4

<400> SEQUENCE: 7

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Ser
            20                  25                  30

Trp Met Asn Trp Val Arg Gln Ala Pro Gly Lys Gly Leu Glu Trp Met
            35                  40                  45

Gly Arg Ile Tyr Pro Gly Asp Gly Gln Thr His Tyr Ala Gln Lys Phe
        50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys

```
                    85                  90                  95
Gly Glu Gly Tyr Leu Asp Pro Met Asp Tyr Trp Gly Gln Gly Thr Leu
            100                 105                 110

Val Thr Val Ser Ser
            115

<210> SEQ ID NO 8
<211> LENGTH: 11
<212> TYPE: PRT
<213> ORGANISM: Artificial Sequence
<220> FEATURE:
<223> OTHER INFORMATION: CAN04 variant 6 Light chain CDR1 (according to
      Chotia)

<400> SEQUENCE: 8

Ser Ala Ser Gln Gly Ile Asn Asn Tyr Leu Asn
1               5                   10

<210> SEQ ID NO 9
<211> LENGTH: 9
<212> TYPE: PRT
<213> ORGANISM: Artificial Sequence
<220> FEATURE:
<223> OTHER INFORMATION: CAN04 variant 6 Light chain CDR2 (according to
      Chotia)

<400> SEQUENCE: 9

Tyr Thr Ser Gly Leu His Ala Gly Val
1               5

<210> SEQ ID NO 10
<211> LENGTH: 9
<212> TYPE: PRT
<213> ORGANISM: Artificial Sequence
<220> FEATURE:
<223> OTHER INFORMATION: CAN04 variant 6 Light chain CDR3 (according to
      Chotia)

<400> SEQUENCE: 10

Gln Gln Tyr Ser Ile Leu Pro Trp Thr
1               5

<210> SEQ ID NO 11
<211> LENGTH: 11
<212> TYPE: PRT
<213> ORGANISM: Artificial Sequence
<220> FEATURE:
<223> OTHER INFORMATION: CAN04 variant 6 Heavy chain CDR1 (according to
      Chotia)

<400> SEQUENCE: 11

Gly Tyr Ala Phe Thr Ser Ser Ser Trp Met Asn
1               5                   10

<210> SEQ ID NO 12
<211> LENGTH: 17
<212> TYPE: PRT
<213> ORGANISM: Artificial Sequence
<220> FEATURE:
<223> OTHER INFORMATION: CAN04 variant 6 Heavy chain CDR2 (according to
      Chotia)

<400> SEQUENCE: 12

Arg Ile Tyr Pro Gly Asp Gly Asn Thr His Tyr Ala Gln Lys Phe Gln
1               5                   10                  15

Gly
```

<210> SEQ ID NO 13
<211> LENGTH: 8
<212> TYPE: PRT
<213> ORGANISM: Artificial Sequence
<220> FEATURE:
<223> OTHER INFORMATION: CAN04 variant 6 Heavy chain CDR3 (according to Chotia)

<400> SEQUENCE: 13

Gly Tyr Leu Asp Pro Met Asp Tyr
1               5

<210> SEQ ID NO 14
<211> LENGTH: 108
<212> TYPE: PRT
<213> ORGANISM: Artificial Sequence
<220> FEATURE:
<223> OTHER INFORMATION: CAN03 variable light chain (VL)

<400> SEQUENCE: 14

Asp Ile Leu Leu Thr Gln Ser Pro Ala Ile Leu Ser Val Ser Pro Gly
1               5                   10                  15

Glu Arg Val Ser Phe Ser Cys Arg Ala Ser Gln Ser Ile Gly Thr Ser
            20                  25                  30

Ile His Trp Tyr Gln Arg Arg Thr Asn Gly Ser Pro Arg Leu Leu Ile
        35                  40                  45

Lys Ser Ala Ser Glu Ser Ile Ser Gly Ile Pro Ser Arg Phe Ser Gly
    50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Ser Asn Ser Trp Pro Thr
                85                  90                  95

Thr Phe Gly Ala Gly Thr Lys Leu Glu Leu Lys Arg
            100                 105

<210> SEQ ID NO 15
<211> LENGTH: 119
<212> TYPE: PRT
<213> ORGANISM: Artificial Sequence
<220> FEATURE:
<223> OTHER INFORMATION: CAN03 variable heavy chain (VH)

<400> SEQUENCE: 15

Asp Val Lys Leu Val Glu Ser Gly Gly Leu Val Lys Pro Gly Gly
1               5                   10                  15

Ser Leu Lys Leu Ser Cys Ala Ala Ser Gly Phe Thr Phe Ser Ile Tyr
            20                  25                  30

Thr Met Ser Trp Val Arg Gln Thr Pro Glu Lys Arg Leu Glu Trp Val
        35                  40                  45

Ala Thr Ile Ser Ile Gly Gly Ser Tyr Ile Asn Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Ile Tyr Tyr Cys
                85                  90                  95

Ser Arg Glu Val Asp Gly Ser Tyr Ala Met Asp Tyr Trp Gly Gln Gly
            100                 105                 110

Thr Ser Val Thr Val Ser Ser
            115

```
<210> SEQ ID NO 16
<211> LENGTH: 11
<212> TYPE: PRT
<213> ORGANISM: Artificial Sequence
<220> FEATURE:
<223> OTHER INFORMATION: CAN03 Light chain CDR1 (according to Chotia)

<400> SEQUENCE: 16

Arg Ala Ser Gln Ser Ile Gly Thr Ser Ile His
1               5                   10

<210> SEQ ID NO 17
<211> LENGTH: 7
<212> TYPE: PRT
<213> ORGANISM: Artificial Sequence
<220> FEATURE:
<223> OTHER INFORMATION: CAN03 Light chain CDR2 (according to Chotia)

<400> SEQUENCE: 17

Ser Ala Ser Glu Ser Ile Ser
1               5

<210> SEQ ID NO 18
<211> LENGTH: 9
<212> TYPE: PRT
<213> ORGANISM: Artificial Sequence
<220> FEATURE:
<223> OTHER INFORMATION: CAN03 Light chain CDR3 (according to Chotia)

<400> SEQUENCE: 18

Gln Gln Ser Asn Ser Trp Pro Thr Thr
1               5

<210> SEQ ID NO 19
<211> LENGTH: 10
<212> TYPE: PRT
<213> ORGANISM: Artificial Sequence
<220> FEATURE:
<223> OTHER INFORMATION: CAN03 Heavy chain CDR1 (according to Chotia)

<400> SEQUENCE: 19

Gly Phe Thr Phe Ser Ile Tyr Thr Met Ser
1               5                   10

<210> SEQ ID NO 20
<211> LENGTH: 17
<212> TYPE: PRT
<213> ORGANISM: Artificial Sequence
<220> FEATURE:
<223> OTHER INFORMATION: CAN03 Heavy chain CDR2 (according to Chotia)

<400> SEQUENCE: 20

Thr Ile Ser Ile Gly Gly Ser Tyr Ile Asn Tyr Pro Asp Ser Val Lys
1               5                   10                  15

Gly

<210> SEQ ID NO 21
<211> LENGTH: 10
<212> TYPE: PRT
<213> ORGANISM: Artificial Sequence
<220> FEATURE:
<223> OTHER INFORMATION: CAN03 Heavy chain CDR3 (according to Chotia)

<400> SEQUENCE: 21

Glu Val Asp Gly Ser Tyr Ala Met Asp Tyr
```

```
1               5                    10
```

<210> SEQ ID NO 22
<211> LENGTH: 7
<212> TYPE: PRT
<213> ORGANISM: Artificial Sequence
<220> FEATURE:
<223> OTHER INFORMATION: CAN04 variant 6 Variable light chain CDR2
      (according to Kabat)

<400> SEQUENCE: 22

Tyr Thr Ser Gly Leu His Ala
1               5

<210> SEQ ID NO 23
<211> LENGTH: 8
<212> TYPE: PRT
<213> ORGANISM: Artificial Sequence
<220> FEATURE:
<223> OTHER INFORMATION: CAN04 variant 6 Variable light chain CDR3
      (according to Kabat)

<400> SEQUENCE: 23

Gln Tyr Ser Ile Leu Pro Trp Thr
1               5

<210> SEQ ID NO 24
<211> LENGTH: 7
<212> TYPE: PRT
<213> ORGANISM: Artificial Sequence
<220> FEATURE:
<223> OTHER INFORMATION: CAN04 variant 6 Variable heavy chain CDR1
      (according to Kabat)

<400> SEQUENCE: 24

Gly Tyr Ala Phe Thr Ser Ser
1               5

<210> SEQ ID NO 25
<211> LENGTH: 6
<212> TYPE: PRT
<213> ORGANISM: Artificial Sequence
<220> FEATURE:
<223> OTHER INFORMATION: CAN04 variant 6 Variable heavy chain CDR2
      (according to Kabat)

<400> SEQUENCE: 25

Tyr Pro Gly Asp Gly Asn
1               5

<210> SEQ ID NO 26
<211> LENGTH: 8
<212> TYPE: PRT
<213> ORGANISM: Artificial Sequence
<220> FEATURE:
<223> OTHER INFORMATION: CAN03 Variable light chain CDR3 (according to
      Kabat)

<400> SEQUENCE: 26

Gln Ser Asn Ser Trp Pro Thr Thr
1               5

<210> SEQ ID NO 27
<211> LENGTH: 7
<212> TYPE: PRT
<213> ORGANISM: Artificial Sequence
<220> FEATURE:
<223> OTHER INFORMATION: CAN03 Variable heavy chain CDR1(according to Kabat)

<400> SEQUENCE: 27

Gly Phe Thr Phe Ser Ile Tyr
1               5

<210> SEQ ID NO 28
<211> LENGTH: 6
<212> TYPE: PRT
<213> ORGANISM: Artificial Sequence
<220> FEATURE:
<223> OTHER INFORMATION: CAN03 Variable heavy chain CDR2 (according to
      Kabat)

<400> SEQUENCE: 28

Ser Ile Gly Gly Ser Tyr
1               5

<210> SEQ ID NO 29
<211> LENGTH: 10
<212> TYPE: PRT
<213> ORGANISM: Artificial Sequence
<220> FEATURE:
<223> OTHER INFORMATION: CAN04 variant 6 Light chain CDR1 (according to
      Kabat)

<400> SEQUENCE: 29

Ala Ser Gln Gly Ile Asn Asn Tyr Leu Asn
1               5                   10

<210> SEQ ID NO 30
<211> LENGTH: 10
<212> TYPE: PRT
<213> ORGANISM: Artificial Sequence
<220> FEATURE:
<223> OTHER INFORMATION: CAN03 Light chain CDR1 (according to Kabat)

<400> SEQUENCE: 30

Ala Ser Gln Ser Ile Gly Thr Ser Ile His
1               5                   10

<210> SEQ ID NO 31
<211> LENGTH: 329
<212> TYPE: PRT
<213> ORGANISM: Artificial Sequence
<220> FEATURE:
<223> OTHER INFORMATION: CAN04 Heavy chain constant region

<400> SEQUENCE: 31

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Leu Tyr Ser Leu
    50                  55                  60

Ser Ser Val Val Thr Val Pro Ser Ser Ser Leu Gly Thr Gln Thr Tyr
65                  70                  75                  80

Ile Cys Asn Val Asn His Lys Pro Ser Asn Thr Lys Val Asp Lys Lys
                85                  90                  95

Val Glu Pro Lys Ser Cys Asp Lys Thr His Thr Cys Pro Pro Cys Pro
            100                 105                 110

```
Ala Pro Glu Leu Leu Gly Gly Pro Ser Val Phe Leu Phe Pro Pro Lys
            115                 120                 125
Pro Lys Asp Thr Leu Met Ile Ser Arg Thr Pro Glu Val Thr Cys Val
130                 135                 140
Val Val Asp Val Ser His Glu Asp Pro Glu Val Lys Phe Asn Trp Tyr
145                 150                 155                 160
Val Asp Gly Val Glu Val His Asn Ala Lys Thr Lys Pro Arg Glu Glu
                165                 170                 175
Gln Tyr Asn Ser Thr Tyr Arg Val Val Ser Val Leu Thr Val Leu His
            180                 185                 190
Gln Asp Trp Leu Asn Gly Lys Glu Tyr Lys Cys Lys Val Ser Asn Lys
        195                 200                 205
Ala Leu Pro Ala Pro Ile Glu Lys Thr Ile Ser Lys Ala Lys Gly Gln
210                 215                 220
Pro Arg Glu Pro Gln Val Tyr Thr Leu Pro Pro Ser Arg Glu Glu Met
225                 230                 235                 240
Thr Lys Asn Gln Val Ser Leu Thr Cys Leu Val Lys Gly Phe Tyr Pro
                245                 250                 255
Ser Asp Ile Ala Val Glu Trp Glu Ser Asn Gly Gln Pro Glu Asn Asn
            260                 265                 270
Tyr Lys Thr Thr Pro Pro Val Leu Asp Ser Asp Gly Ser Phe Phe Leu
        275                 280                 285
Tyr Ser Lys Leu Thr Val Asp Lys Ser Arg Trp Gln Gln Gly Asn Val
290                 295                 300
Phe Ser Cys Ser Val Met His Glu Ala Leu His Asn His Tyr Thr Gln
305                 310                 315                 320
Lys Ser Leu Ser Leu Ser Pro Gly Lys
                325

<210> SEQ ID NO 32
<211> LENGTH: 106
<212> TYPE: PRT
<213> ORGANISM: Artificial Sequence
<220> FEATURE:
<223> OTHER INFORMATION: CAN04 Light chain constant region

<400> SEQUENCE: 32

Thr Val Ala Ala Pro Ser Val Phe Ile Phe Pro Pro Ser Asp Glu Gln
1               5                   10                  15
Leu Lys Ser Gly Thr Ala Ser Val Val Cys Leu Leu Asn Asn Phe Tyr
            20                  25                  30
Pro Arg Glu Ala Lys Val Gln Trp Lys Val Asp Asn Ala Leu Gln Ser
        35                  40                  45
Gly Asn Ser Gln Glu Ser Val Thr Glu Gln Asp Ser Lys Asp Ser Thr
    50                  55                  60
Tyr Ser Leu Ser Ser Thr Leu Thr Leu Ser Lys Ala Asp Tyr Glu Lys
65                  70                  75                  80
His Lys Val Tyr Ala Cys Glu Val Thr His Gln Gly Leu Ser Ser Pro
                85                  90                  95
Val Thr Lys Ser Phe Asn Arg Gly Glu Cys
            100                 105

<210> SEQ ID NO 33
<211> LENGTH: 320
<212> TYPE: PRT
<213> ORGANISM: Homo sapiens
<220> FEATURE:
```

<223> OTHER INFORMATION: CAN03 Heavy chain constant region, Ig gamma-1
      chain C region (UnitProt Accession No. P01857)

<400> SEQUENCE: 33

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320
```

<210> SEQ ID NO 34
<211> LENGTH: 106
<212> TYPE: PRT
<213> ORGANISM: Homo sapiens
<220> FEATURE:
<223> OTHER INFORMATION: CAN03 Light chain constant region, Ig kappa
      chain C region (UnitProt Accession No. P01834)

<400> SEQUENCE: 34

```
Thr Val Ala Ala Pro Ser Val Phe Ile Phe Pro Pro Ser Asp Glu Gln
1               5                   10                  15
```

```
Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105
```

<210> SEQ ID NO 35
<211> LENGTH: 447
<212> TYPE: PRT
<213> ORGANISM: Artificial Sequence
<220> FEATURE:
<223> OTHER INFORMATION: hu3F8-HC-hIgG1-K409R

<400> SEQUENCE: 35

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Thr Ser Ser
            20                  25                  30

Trp Met Asn Trp Val Arg Gln Ala Pro Gly Gln Gly Leu Glu Trp Met
        35                  40                  45

Gly Arg Ile Tyr Pro Gly Asp Gly Asn Thr His Tyr Ala Gln Lys Phe
    50                  55                  60

Gln Gly Arg Val Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Gly Glu Gly Tyr Leu Asp Pro Met Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270
```

```
Val Lys Phe Asn Trp Tyr Val Asp Gly Val Glu Val His Asn Ala Lys
            275                 280                 285

Thr Lys Pro Arg Glu Glu Gln Tyr Asn Ser Thr Tyr Arg Val Val Ser
        290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 36
<211> LENGTH: 214
<212> TYPE: PRT
<213> ORGANISM: Artificial Sequence
<220> FEATURE:
<223> OTHER INFORMATION: hu3F8-LC-hk

<400> SEQUENCE: 36

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Gly Ile Asn Asn Tyr
            20                  25                  30

Leu Asn Trp Tyr Gln Gln Lys Pro Gly Lys Ala Pro Lys Leu Leu Ile
        35                  40                  45

His Tyr Thr Ser Gly Leu His Ala Gly Val Pro Ser Arg Phe Ser Gly
    50                  55                  60

Ser Gly Ser Gly Thr Asp Tyr Thr Leu Thr Ile Ser Ser Leu Glu Pro
65                  70                  75                  80

Glu Asp Val Ala Thr Tyr Tyr Cys Gln Gln Tyr Ser Ile Leu Pro Trp
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190
```

```
Ala Cys Glu Val Thr His Gln Gly Leu Ser Ser Pro Val Thr Lys Ser
            195                 200                 205

Phe Asn Arg Gly Glu Cys
    210

<210> SEQ ID NO 37
<211> LENGTH: 449
<212> TYPE: PRT
<213> ORGANISM: Artificial Sequence
<220> FEATURE:
<223> OTHER INFORMATION: ch2C9-HC-hIgG1-F405L

<400> SEQUENCE: 37

Asp Val Lys Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Ile Tyr
            20                  25                  30

Thr Met Ser Trp Val Arg Gln Thr Pro Glu Lys Arg Leu Glu Trp Val
        35                  40                  45

Ala Thr Ile Ser Ile Gly Gly Ser Tyr Ile Asn Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Ile Tyr Tyr Cys
                85                  90                  95

Ser Arg Glu Val Asp Gly Ser Tyr Ala Met Asp Tyr Trp Gly Gln Gly
            100                 105                 110

Thr Ser Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335
```

```
Thr Ile Ser Lys Ala Lys Gly Gln Pro Arg Glu Pro Gln Val Tyr Thr
            340                 345                 350
Leu Pro Pro Ser Arg Glu Glu Met Thr Lys Asn Gln Val Ser Leu Thr
            355                 360                 365
Cys Leu Val Lys Gly Phe Tyr Pro Ser Asp Ile Ala Val Glu Trp Glu
370                 375                 380
Ser Asn Gly Gln Pro Glu Asn Asn Tyr Lys Thr Thr Pro Pro Val Leu
385                 390                 395                 400
Asp Ser Asp Gly Ser Phe Leu Leu Tyr Ser Lys Leu Thr Val Asp Lys
                405                 410                 415
Ser Arg Trp Gln Gln Gly Asn Val Phe Ser Cys Ser Val Met His Glu
            420                 425                 430
Ala Leu His Asn His Tyr Thr Gln Lys Ser Leu Ser Leu Ser Pro Gly
            435                 440                 445
Lys
```

```
<210> SEQ ID NO 38
<211> LENGTH: 214
<212> TYPE: PRT
<213> ORGANISM: Artificial Sequence
<220> FEATURE:
<223> OTHER INFORMATION: ch2C9-LC-hk

<400> SEQUENCE: 38

Asp Ile Leu Leu Thr Gln Ser Pro Ala Ile Leu Ser Val Ser Pro Gly
1               5                   10                  15
Glu Arg Val Ser Phe Ser Cys Arg Ala Ser Gln Ser Ile Gly Thr Ser
            20                  25                  30
Ile His Trp Tyr Gln Arg Arg Thr Asn Gly Ser Pro Arg Leu Leu Ile
            35                  40                  45
Lys Ser Ala Ser Glu Ser Ile Ser Gly Ile Pro Ser Arg Phe Ser Gly
50                  55                  60
Ser Gly Ser Gly Thr Asp Phe Thr Leu Ser Ile Asn Ser Val Glu Ser
65                  70                  75                  80
Glu Asp Ile Ala Asp Tyr Tyr Cys Gln Gln Ser Asn Ser Trp Pro Thr
                85                  90                  95
Thr Phe Gly Ala Gly Thr Lys Leu Glu Leu Lys Arg Thr Val Ala Ala
            100                 105                 110
Pro Ser Val Phe Ile Phe Pro Pro Ser Asp Glu Gln Leu Lys Ser Gly
            115                 120                 125
Thr Ala Ser Val Val Cys Leu Leu Asn Asn Phe Tyr Pro Arg Glu Ala
130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
            195                 200                 205
Phe Asn Arg Gly Glu Cys
210
```

ANTI-IL1RAP ANTIBODY COMPOSITIONS

This application is a 371 National Phase of International Application No. PCT/EP2019/071974, filed on Aug. 15, 2019, which claims the benefit of Swedish Patent Application No. 1850983-6, filed Aug. 16, 2018, which are incorporated herein by reference for all purposes.

The instant application contains a Sequence Listing which has been submitted electronically in ASCII format and is hereby incorporated by reference in its entirety. Said ASCII copy, created on Oct. 21, 2021, is named 2021-10-21_01177-0003-00US_Sequence Listing_corrected.txt and is 33,587 bytes in size.

FIELD OF INVENTION

The present invention relates to antibodies directed to Interleukin 1 Receptor Accessory Protein (IL1RAP) and their use in the treatment and diagnosis of diseases associated with IL1RAP, such as inflammatory disorders, autoimmune disorders and neoplastic disorders.

BACKGROUND OF INVENTION

Inflammatory and autoimmune disorders, and to a certain degree also neoplastic disorders, all have an aetiology related to cytokine mediated inflammation. The Interleukin-1 family of cytokines is believed to be of particular relevance for the aetiology of these indications.

Interleukin-1 Receptor Associated Protein in Interleukin-1 Family Signal Transduction The Interleukin-1 (IL-1) family of cytokines include IL-1α, IL-1β, IL-18, IL-33, IL-36α, IL-36β and IL-36γ. These cytokines have structural relations and mediate pro-inflammatory effects. Each cytokine binds a specific receptor that in turn dimerizes with a co-receptor leading to signal transduction. Signaling through these receptor complexes involve the MyD88 adaptor protein and subsequent NFκB activation. In addition to the pro-inflammatory cytokines above, the IL-1 family also include two receptor antagonists, IL-1Ra and IL-36Ra, that compete with IL-1 and IL-36 respectively for binding to their receptors. Binding of the receptor antagonists is non-productive and does not induce a signal.

IL1RAP is the co-receptor for the interleukin-1 receptor (IL1R1), the IL-33 receptor (ST2) and the IL-36 receptor (IL1Rrp2) and is critical for for mediating the effects of these cytokines (Garlanda et al, Immunity. 2013-12-12; 39(6):1003-18). The structure of the IL-1 receptor with IL1RAP has been solved (Wang, D., et al., Nat Immunol 2010 11(10):905-11, Thomas, C., et al., Nat Struct Mol Biol 2012 19(4):455-7) and the interaction between IL1RAP and ST2 or IL1Rrp2 are most likely very similar to the IL1R1-IL1RAP interaction (Liu, X. et al., PNAS 2013 110(37): 14918-23, Gunther, S. et al., J. Immunol. 2014 193:921-30).

Antibodies generated towards IL1RAP have the ability to block IL1RAP-mediated signaling (Järàs, M., et al., PNAS 2010 107(37):16280-5, FIG. 3). The binding epitope is crucial for the effect, since not all antibodies have the ability to block signaling even though they have the ability to bind IL1RAP and mediate efficient ADCC (Ågerstam, H. et al., PNAS 2015 112(34):10786-91).

Anti-IL1RAP antibodies that bind to different domains of IL1RAP are known from WO 2015/132602 and WO 2016/020502. Of these, CAN03 and CAN04 bind to domain 3 and 2 respectively and both show complete inhibition of IL-1 signaling and partial inhibition of IL-33 signaling.

Interleukin-1 Biology

Interleukin-1 (IL-1) is a potent pro-inflammatory cytokine that can be produced by a variety of cell types, including mononuclear phagocytes, in response to infection and inflammation. The IL-1 family consists of seven agonists, including IL-1α and IL-1β, and three naturally occurring receptor antagonists, including the IL-1 receptor antagonist (IL-1Ra) (Dinarello, CA, Blood 1996, 87(6):2095-147). Two IL-1 receptors, IL-1R type I and IL-1R type II, have been identified. Both receptors can interact with all three forms of the IL-1 family molecules. IL-1RI is responsible for mediating IL-1-induced cellular activation. However, the IL-1/IL-1RI complex cannot signal by itself, but is dependent on association with a second receptor chain, IL-1R Accessory Protein (IL1RAP) (Dinarello, CA, Blood 1996, 87(6):2095-147). In contrast to IL-1RI, IL-1RII does not induce cellular activation upon binding to IL-1 and thus IL-1RII functions as regulatory decoy receptor, leading to a net decrease in IL-1 available to bind to IL-1RI.

IL-1 is a potent pro-inflammatory cytokine, which is induced at sites of local infection or inflammation and is involved in the regulation of a variety of physiological and cellular events (summarised in Dinarello CA, CHEST, 2000, 118:503-508 and Dinarello, CA, Clin Exp Rheumatol, 2002, 20(5 Suppl 27): S1-13). It is capable of activating several cell types including leukocytes and endothelial cells. IL-1 induces and amplifies immunological responses by promoting the production and expression of adhesion molecules, cytokines, chemokines and other inflammatory mediators such as prostaglandin $E_2$ and nitric oxide (NO). As a consequence, local inflammation is amplified and sustained. In addition, the IL-1-induced production of inflammatory mediators results in fever, headache, hypotension and weight loss. Furthermore, IL-1 is a hematopoietic growth factor and has been shown to reduce the nadir of leukocytes and platelets in patients during bone marrow transplantation. IL-1 has also been shown to promote angiogenesis by inducing the production of vascular endothelial growth factor, thereby promoting pannus formation and blood supply in rheumatic joints. Finally, IL-1 has been shown to promote the bone and cartilage degradation in rheumatic diseases.

IL-1 is implicated in a wide range of diseases and conditions ranging from gout to cancer (for reviews, see Dinarello et al., 2012, Nature Reviews 11:633-652 and Dinarello, 2014, Mol. Med. 20 (suppl. 1): S43-S58; the disclosures of which are incorporated herein by reference), including:

Joint, bone and muscle diseases, such as rheumatoid arthritis and osteoarthritis;

Hereditary systemic autoinflammatory diseases, such as familial Mediterranean fever;

Systemic autoinflammatory diseases, such as systemic juvenile idiopathic arthritis and adult-onset Still's disease;

Common inflammatory diseases, such as gout and type 2 diabetes;

Acute-onset ischemic diseases, such as myocardial infarction; and

Cancer.

A number of therapies for blocking IL-1 activity are approved and in development. Targeting IL-1 began in 1993 with the introduction of anakinra (Kineret; Amgen), a recombinant form of the naturally occurring IL-1 receptor antagonist (IL-1Ra), which blocks the activity of both IL-1α and IL-1β; this therapeutic has since been used to demonstrate a role for IL-1 in numerous diseases (see above).

Anakinra currently dominates the field of IL-1 therapeutics owing to its good safety record, short half-life and multiple routes of administration. Neutralising IL-1 with antibodies or soluble receptors has also proved to be effective, and the soluble decoy receptor rilonacept (Arcalyst; Regeneron) and the anti-IL-1β neutralizing monoclonal antibody canakinumab (Ilaris; Novartis) have been approved. Other therapeutic approaches, including IL-1α neutralisation, a therapeutic vaccine targeting IL-1β and a chimeric IL-1Ra, are in early clinical trials. In addition, orally active small-molecule inhibitors of IL-1 production, such as caspase 1 inhibitors, have been developed and are being tested Interleukin-33 Biology Interleukin-33 (IL-33) was identified as an IL-1 family member that induced type 2 immune responses (Schmitz, J., et al., Immunity 2005 23:479-90) by activating cells like T helper 2 (TH2) cells and mast cells. Subsequent studies have however expanded the roles of IL-33 and it is now considered to have other pro-inflammatory effects as well (Yew Liew, F., et al., Nat Rev Immunol 2016 16:676-89). IL-33 is released by damaged or necrotic cells as a stress signal, a so called alarmin, and exerts its effects by binding to its receptor ST2. Binding of IL-33 to ST2 recruits IL1RAP and signaling through MYD88 is induced. A soluble form of ST2 exist that has been suggested to act as a decoy receptor. Interestingly, IL-33 has potent pro-inflammatory roles at the same time as it induces cells that limit the immune response and induce tissue repair, such as $T_{reg}$ and M2 macrophages.

IL-33 is involved in inflammatory diseases both as an inflammatory mediator released through stress or cell death or from failing of inducing regulatory responses (such as induction of $T_{reg}$ and M2 macrophages). IL-33 has been coupled to a number of diseases (for review see Yew Liew, F., et al., Nat Rev Immunol 2016 16:676-89) such as:

Asthma

Allergic diseases such as allergic rhinitis and atopic dermatitis

Cardiovascular diseases

Rheumatoid arthritis

IBD

Diabetes and obesity

COPD

Cancer

Development of IL-33 inhibitory antibodies are ongoing (Pfizer, Johnson&Johnson) and clinical trials targeting IL-33 function has been initiated in asthma and atopic dermatitis.

Interleukin-36 Biology

IL1Rrp2 is expressed on human monocytes and dendritic cells which are induced by IL-36 cytokines to produce a number of inflammatory cytokines (Foster, A. M., et al., J Immunol 2014 192:6053-61, Mutamba, S., et al., Eur J Immunol 2012 42:607-17). IL-36 has received special attention in skin diseases such as psoriasis where there is evidence that IL-36 act upstream to induce a number of other pathological cytokines (for review see Gabay C. and Owne, E., J Leukocyte Biol 2015 97:645-52). Treatment of mice with antibodies that block IL1Rrp2 function lead to reduction of skin pathology in immunodeficient mice transplanted with human psoriatic skin (Blumberg. H., et al., J Immunol 2010 185:4354-62) and a severe life-threatening form of psoriasis (GPP) is caused by a mutation in a natural IL-36 receptor antagonist (IL-36Ra). Reports also support a function of IL-36 cytokines in lung pathology, including COPD and asthma, but the role of these cytokines in these diseases is less clear.

Current treatments of inflammatory and autoimmune diseases are not able to inhibit the key cytokines described above, in a concerted manner.

SUMMARY OF INVENTION

The present inventors have developed novel antibodies and antibody compositions that have been found to block IL1RAP-mediated signalling via key inflammatory cytokines, in a concerted and synergistic manner. This unexpected property makes the agents of the present invention particularly suitable for treatment of inflammatory and autoimmune diseases and other conditions associated with IL1RAP and/or responsive to inhibition of IL-1 signalling, IL-33 signalling and/or IL-36 signalling.

In one aspect, the present invention concerns a composition comprising at least a first binding agent with specificity for anti-Interleukin-1 Receptor Accessory Protein (IL1RAP) and a second binding agent with specificity for IL1RAP, wherein the first and second binding agents bind to at least two different extracellular domains of IL1RAP.

In another aspect, the present invention concerns a bi-epitopic binding agent comprising:

a first antigen-binding region, and a second antigen binding region, wherein the first antigen binding region and the second antigen binding region bind to different extracellular domains of human interleukin-receptor accessory protein (IL1RAP).

In one aspect, the present invention concerns a composition comprising one or more polynucleotides, which, collectively or individually, encode either (i) first and second binding agents or (ii) a bi-epitopic binding agent as defined herein. In another aspect, the present invention concerns an isolated polynucleotide encoding either (i) first and second binding agents or (ii) a bi-epitopic binding agent as defined herein. In yet another aspect, the present invention concerns an expression vector comprising one or more polynucleotides which, collectively or individually, encode either (i) first and second binding agents or (ii) a bi-epitopic binding agent as defined herein. In yet another aspect, the current invention concerns a host cell comprising one or more polynucleotides which, collectively or individually, encode either (i) first and second binding agents or (ii) a bi-epitopic antibody as defined herein. In yet another aspect, the current invention concerns a host cell comprising one or more expression vectors as described herein.

In one aspect, the current invention concerns a composition comprising at least two binding agents; or a bi-epitopic binding agent; or a polynucleotide; or a vector; or a host cell; or a pharmaceutical composition as described herein for use as a medicament.

In one aspect, the current invention concerns a composition comprising at least two binding agents; or a bi-epitopic binding agent; or a polynucleotide; or a vector; or a host cell; or a pharmaceutical composition as described herein for use as a diagnostic and/or prognostic agent.

In one aspect, the current invention concerns a composition comprising at least two binding agents; or a bi-epitopic binding agent; or a polynucleotide; or a vector; or a host cell; or a pharmaceutical composition as described herein for use in the treatment, amelioration, prevention, diagnosis or prognosis of a IL1RAP-associated disease or disorder.

DETAILED DESCRIPTION OF THE INVENTION

Figure 1:
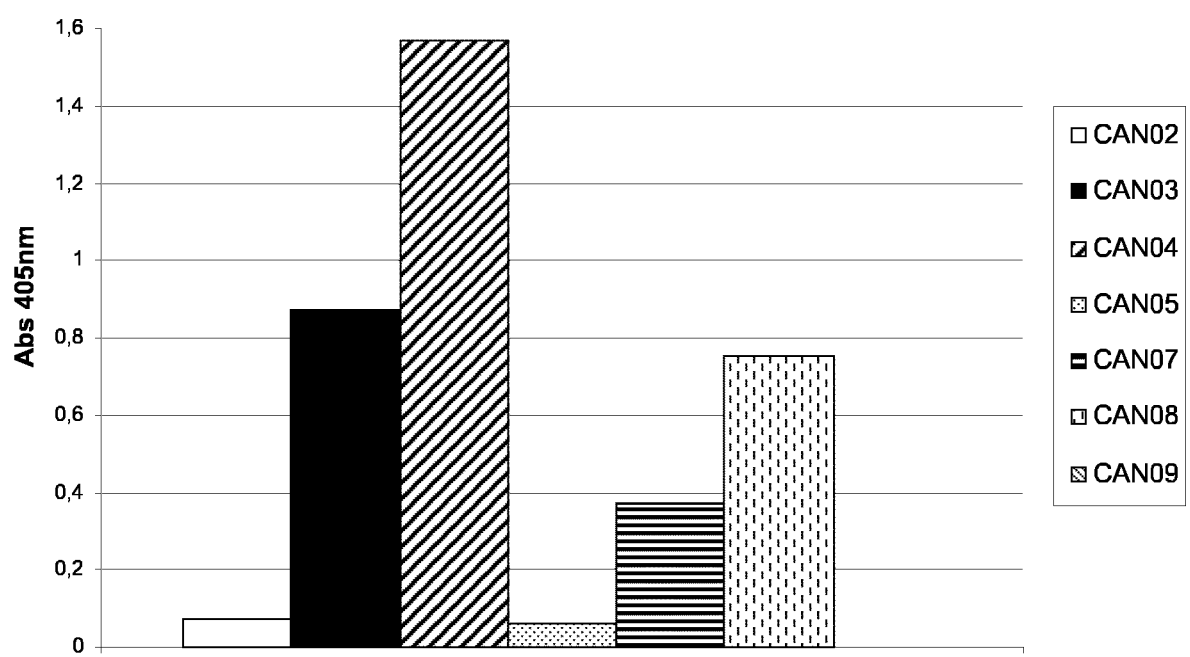
FIG. 1. Binding of exemplary antibodies in an indirect ELISA to human IL-1RAP. The exemplary antibodies of the invention, CAN03 and CAN04, was found to possess the highest affinities for human IL-1RAP.

The invention is as defined in the claims.

Definitions

The term "agent" as herein refers to a compound or substance capable of interacting with interleukin-1 accessory protein (IL1RAP). The agent is as defined in the claims, preferably an antibody, an antibody-mimetic or a composition of antibodies.

The term "affinity-matured antibody" refers to an antibody with one or more alterations in one or more HVRs thereof which result in an improvement in the affinity of the antibody for antigen, compared to a parent antibody which does not possess those alteration(s).

Preferred affinity-matured antibodies will have nanomolar or even picomolar affinities for the target antigen. The technique of affinity maturation provides a method for enhancing antigen-neutralizing ability of an antibody and may increase the antigen-binding activity by introducing mutation(s) into amino acid residue(s) in the CDRs and/or framework regions of an antibody variable domain. Improving the antigen-binding properties of an antibody may improve the biological activity of the antibody in vitro or reduce the dosage, and may further improve the efficacy in vivo (in the body).

The term "amino acid" as used herein includes the standard twenty genetically-encoded amino acids and their corresponding stereoisomers in the 'D' form (as compared to the natural 'L' form), omega-amino acids and other naturally-occurring amino acids, unconventional amino acids (e.g. α,α-disubstituted amino acids, N-alkyl amino acids, etc.) and chemically derivatised amino acids (see below).

When an amino acid is being specifically enumerated, such as "alanine" or "Ala" or "A", the term refers to both L-alanine and D-alanine unless explicitly stated otherwise. Other unconventional amino acids may also be suitable components for polypeptides of the present invention, as long as the desired functional property is retained by the polypeptide. For the peptides shown, each encoded amino acid residue, where appropriate, is represented by a single letter designation, corresponding to the trivial name of the conventional amino acid.

In one embodiment, the antibody polypeptides as defined herein comprise or consist of L-amino acids.

The term "bi-epitopic antibody" is an antibody with specificity for two different epitopes of the same antigen, such as wherein the two epitopes are different domains of IL1RAP.

Bi-epitopic antibodies can be prepared as full-length antibodies or low molecular weight forms thereof (e.g. F(ab')2 bi-epitopic antibodies, sc(Fv)2 bi-epitopic antibodies, diabody bi-epitopic antibodies, tri-bodies and miniantibodies).

Methods for making bi-epitopic antibodies are known in the art. Traditionally, the recombinant production of bi-epitopic antibodies is based on the co-expression of two immunoglobulin heavy-chain/light-chain pairs, where the two heavy chains have different specificities [Milstein and Cuello, Nature, 305:537-539 (1983)]. Because of the random assortment of immunoglobulin heavy and light chains, these hybridomas (quadromas) produce a potential mixture of ten different antibody molecules, of which only one has the correct bispecific structure. Further improvements of the quadroma technique has been made through creation of chimeric quadroma which facilitates enrichment of antibody with correct bi-epitopic structure (Lindhofer et al. Immunol. 155:219-225 (1995). The purification of the correct molecule is usually accomplished by affinity chromatography steps. Similar procedures are disclosed in WO 93/08829, published 13-5-1993, and in Traunecker et al., EMBO J., 10:3655-3659 (1991).

Antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transfected into a suitable host organism. For further details of generating bispecific antibodies see, for example, Suresh et al., Methods in Enzymology, 121:210 (1986).

According to another approach described in WO 96/27011, the interface between a pair of antibody molecules can be engineered to maximize the percentage of heterodimers which are recovered from recombinant cell culture. The preferred interface comprises at least a part of the CH3 region of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bi-epitopic antibodies can be prepared as full length antibodies or antibody fragments (e.g. F(ab')2 bi-epitopic antibodies).

Techniques for generating bispecific antibodies from antibody fragments have been described in the literature. For example, bi-epitopic antibodies can be prepared using chemical linkage. Brennan et al., Science 229:81 (1985) describe a procedure wherein intact antibodies are proteolytically cleaved to generate F(ab')2 fragments. Bi-epitopic antibodies can in one embodiment be considered as a type of bispecific antibody, and can thus be prepared in the same manner as bispecific antibodies. The fragments referred to herein above are reduced in the presence of the dithiol complexing agent sodium arsenite to stabilize vicinal di thiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bi-epitopic antibody. The bi-epitopic antibodies produced can be used as agents for the selective immobilization of enzymes.

Fab' fragments may be directly recovered from *E. coli* and chemically coupled to form bi-epitopic antibodies. Shalaby et al., J. Exp. Med. 175:217-225 (1992) describe the production of a fully humanized bispecific antibody F(ab')2 molecule. Each Fab' fragment was separately secreted from *E. coli* and subjected to directed chemical coupling in vitro to form the bi-epitopic antibody. The bi-epitopic antibody thus formed was able to bind to cells overexpressing the ErbB2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bi-epitopic antibodies have been produced using leucine zippers. Kostelny et al., J. Immunol. 148 (5): 1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., Proc. Natl. Acad. Sci. USA 90:6444-6448 (1993) has provided an alternative mechanism for making bispecific antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See, Gruber et al., J. Immunol. 152:5368 (1994). Antibodies with more than two valencies are contemplated. For example, trispecific antibodies can be prepared. Tutt et al., J. Immunol. 147:60 (1991). A more recent approach for manufacturing bispecific antibodies is described in Kontermann & Brinkmann, (2015) Drug Discovery Today 20 (7). The methods described therein can directly be applied by those of skill in the art for producing bi-epitopic antibodies.

Another method of making and using bispecific or multispecific constructs is known as the dock-and-lock technology (U.S. patent application Ser. No. 11/389,358, filed Mar. 24, 2006; Ser. No. 11/391,584, filed Mar. 28, 2006; Ser. No. 11/478,021, filed Jun. 29, 2006; Ser. No. 11/633,729, filed Dec. 5, 2006). The DNL bispecific antibodies are designed by utilizing the specific interaction between the regulatory (R) subunits of cAMP-dependent protein kinase (PKA) and the anchoring domains of A kinase anchor proteins (AKAPs), the mechanism of which has been applied in generation of bioactive conjugates of distinct protein and nonprotein molecules. The generated bispecific antibody is without a Fc region, and has a rather short half-life suitable for pre-targeting approaches.

Another approach is the generation of dual-variable-domain Immunoglobulin (DVD-Ig) antibodies which combines the variable regions from two different antibodies in tandem by naturally occurring linkers. The binding affinity of both variable regions can be preserved and function independently without significant steric hindrance (Wu C. et al., Nat, Biotechnol. 25; 1290-1297 (2007). This approach has been used to generate antibodies which simultaneously bind IL-1α and IL-1β (Wu C. et al. MAbs 1:339-347 (2009).

The term "extracellular domain" as used herein refers to a domain of IL1RAP which is located extracellularly, in whole or in part, when IL1RAP forms a cell membrane-bound complex with an IL1 receptor (e.g. IL1R type I or type II). In human IL1RAP, three extracellular domains are known to exist:

Domain 1: Amino acids 21 to 134
Domain 2: Amino acids 135 to 234
Domain 3: Amino acids 235 to 367

(wherein the amino acid numbering is according to Accession No. Q9NPH3 within UniProtKB/Swiss-Prot).

The structure of IL1RAP is further defined in Wang et al., 2010, *Nature Immunology*, 11:905-912 (the disclosures of which are incorporated herein by reference; see also Example C below).

Thus, the first or second binding agent of the compositions of the invention, or the first or second antigen-binding region of the bi-epitopic antibodies of the invention, may have specificity for domain 1 of IL1RAP. For example, the epitope to which the antibody or antigen-binding fragment binds may be located within amino acids 21 to 39, 40 to 59, 60, to 79, 80, to 99, 100 to 119, or between amino acids 120 to 134 of IL1RAP. However, it will be appreciated that the epitope may be non-linear.

In addition, or alternatively, the first or second binding agent of the compositions of the invention, or the first or second antigen-binding region of the bi-epitopic antibodies of the invention, may have specificity for domain 2 of IL1RAP. For example, the epitope to which the antibody or antigen-binding fragment binds may be located within amino acids 135 to 154, 155 to 174, 175 to 194, 195 to 214 or between amino acids 215 to 234 of IL1RAP. However, it will be appreciated that the epitope may be non-linear.

In addition, or alternatively, the first or second binding agent of the compositions of the invention, or the first or second antigen-binding region of the bi-epitopic antibodies of the invention, may have specificity for domain 3 of IL1RAP. For example, the epitope to which the antibody or antigen-binding fragment binds may be located within amino acids 235 to 249, 250 to 269, 270 to 289, 290, to 309, 310, to 329, 330, to 349 or between amino acids 350 to 367 of IL1RAP. However, it will be appreciated that the epitope may be non-linear.

The term "sequence identity" as used herein refers to a comparative measure of two amino acid or polynucleotide sequences. The level of sequence identity indicates the likelihood that a first sequence is derived from a second sequence. Amino acid sequence identity requires identical amino acid sequences between two aligned sequences. Thus, a candidate sequence sharing 70% amino acid identity with a reference sequence, requires that, following alignment, 70% of the amino acids in the candidate sequence are identical to the corresponding amino acids in the reference sequence. Identity may be determined by aid of computer analysis, such as, without limitations, the ClustalW computer alignment program (Higgins D., Thompson J., Gibson T., Thompson J. D., Higgins D. G., Gibson T. J., 1994. CLUSTAL W: improving the sensitivity of progressive multiple sequence alignment through sequence weighting, position-specific gap penalties and weight matrix choice. Nucleic Acids Res. 22:4673-4680), and the default parameters suggested therein. The ClustalW software is available as a ClustalW WWW Service at the European Bioinformatics Institute from www.ebi.ac.uk. Using this program with its default settings, the mature (bioactive) part of a query and a reference polypeptide are aligned. The number of fully conserved residues are counted and divided by the length of the reference polypeptide.

The ClustalW algorithm may similarly be used to align nucleotide sequences. Sequence identities may be calculated in a similar way as indicated for amino acid sequences.

Antibodies and Antigen Binding Fragments

In one embodiment, one or both of said binding agents are individually an antibody or an antigen binding fragment.

By "an antibody or an antigen-binding fragment" we include substantially intact antibody molecules, as well as chimeric antibodies, humanised antibodies, isolated human antibodies, single chain antibodies, bi-epitopic antibodies, bispecific antibodies, antibody heavy chains, antibody light chains, homodimers and heterodimers of antibody heavy and/or light chains, and antigen-binding fragments and derivatives of the same. Suitable antigen-binding fragments and derivatives include, but are not necessarily limited to, Fv fragments (e.g. single chain Fv and disulphide-bonded Fv), Fab-like fragments (e.g. Fab fragments, Fab' fragments and F(ab)$_2$ fragments), single variable domains (e.g. $V_H$ and $V_L$ domains) and domain antibodies (dAbs, including single and dual formats [i.e. dAb-linker-dAb]). The potential advantages of using antibody fragments, rather than whole antibodies, are several-fold. The smaller size of the fragments may lead to improved pharmacological properties, such as better penetration of solid tissue. Moreover, antigen-binding fragments such as Fab, Fv, ScFv and dAb antibody fragments can be expressed in and secreted from *E. coli*, thus allowing the facile production of large amounts of the said fragments.

The term "antibody" refers to an immunoglobulin molecule, a fragment of an immunoglobulin molecule, or a derivative of either thereof. The term "immunoglobulin molecule" in turn refers to a class of structurally related glycoproteins consisting of two pairs of polypeptide chains, one pair of light (L) low molecular weight chains and one pair of heavy (H) chains, all four inter-connected by disulfide bonds. Each heavy chain typically is comprised of a heavy chain variable region ($V_H$) and a heavy chain constant region ($C_H$). The heavy chain constant region typically is comprised of three domains, $C_H1$, $C_H2$, and $C_H3$. Each light chain typically is comprised of a light chain variable region ($V_L$) and a light chain constant region ($C_L$). The light chain constant region typically is comprised of one domain, $C_L$. The $V_H$ and $V_L$ regions may be further subdivided into regions of hypervariability (or hypervariable regions which may be hypervariable in sequence and/or form of structurally defined loops), also termed complementarity determining regions (CDRs), interspersed with regions that are more conserved, termed framework regions (FRs). Each $V_H$ and $V_L$ is typically composed of three CDRs and four FRs, arranged from amino-terminus to carboxy-terminus in the following order: FR1, CDR1, FR2, CDR2, FR3, CDR3, FR4.

The term "antigen" refers to a molecule comprising at least one epitope. The antigen may for example be a polypeptide, polysaccharide, protein, lipoprotein or glycoprotein.

The term "antigen-binding fragment" refers to fragments of antibodies retaining the ability to specifically bind to an antigen.

A "bi-epitopic antibody" as used herein refers to an antibody capable of binding to two different epitopes simultaneously. A bi-epitopic antibody may be a bispecific antibody. A "bispecific antibody" as used herein refers to an antibody capable of binding to two different epitopes on two different molecules.

The term "chimeric antibody" refers to antibodies comprising regions derived from different species. The chimeric antibody may for example comprise variable regions from one animal species and constant regions from another animal species. For example, a chimeric antibody can be an antibody having variable regions which derive from a mouse monoclonal antibody and constant regions which are human. Such antibodies may also be referred to as humanised antibodies.

The antigen binding fragment of an antibody may also be a "diabody", which are small antibody fragments with two antigen-binding sites. Diabodies preferably comprises a heavy chain variable domain ($V_H$) connected to a light chain variable domain ($V_L$) in the same polypeptide chain ($V_H$-$V_L$).

The term "domain antibodies" (dAbs) refers to antigen-binding fragments of antibodies, preferably ranging from 11 kDa to 15 kDa.

The term "dual-variable-domain antibody" refers to antibody molecules with two different binding specificities. Each light and heavy chain contains two different variable regions joined by short linker sequences. The N-terminal variable regions of the heavy and light chains are of one binding specificity, and the adjacent variable regions of the same heavy and light chains are of a different specificity.

These extended heavy and light chains are synthesized and assembled into covalent molecules containing two heavy chains and two light chains.

The term "epitope" refers to a determinant capable of specific binding to an antibody. Epitopes may for example be comprised within polypeptides, polysaccharide, proteins, lipoproteins or glycoproteins. Epitopes usually consist of chemically active surface groupings of molecules such as amino acids or sugar side chains and usually have specific three dimensional structural characteristics, as well as specific charge characteristics. Epitopes may be conformational or non-conformational, wherein binding to the former but not the latter is lost in the presence of denaturing solvents. Epitopes may be continuous or discontinuous, wherein a discontinuous epitope is a conformational epitope on a protein antigen which is formed from at least two separate regions in the primary sequence of the protein.

The term "Fab fragment" refers to an antigen-binding fragment of an antibody, consisting of one constant and one variable domain of each of the heavy and the light chain.

The term "humanized antibodies" refers to antibodies from non-human species whose protein sequences have been modified to increase their similarity to antibody variants produced naturally in humans.

The antibody according to the invention may be a human or a humanized antibody. A human antibody as used herein is an antibody, which is obtained from a system using human immunoglobulin sequences. Human antibodies may for example be antibodies isolated from an animal (e.g., a mouse) that is transgenic or transchromosomal for human immunoglobulin genes or a hybridoma prepared therefrom. Human antibodies may also be isolated from a host cell transformed to express the antibody, e.g., from a transfectoma. Human antibodies may also be isolated from a recombinant, combinatorial human antibody library.

Human antibodies have variable and constant regions derived from human germline immunoglobulin sequences. In certain embodiments, however, such recombinant human antibodies can be subjected to in vitro mutagenesis or in vivo somatic mutagenesis and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

A human antibody is preferably at least 90%, more preferably at least 95%, even more preferably at least 96%, 97%, 98%, or 99% identical in amino acid sequence to the amino acid sequence encoded by a wild type human immunoglobulin gene.

Said transgenic of transchromosomal animal may contain a human immunoglobulin gene miniloci that encodes unrearranged human heavy (μ and/or γ) and κ light chain immunoglobulin sequences. Furthermore, the animal may contain one or more mutations that inactivate the endogenous heavy and light chain loci. Examples of such animals are described in Lonberg, N. et al. (1994) Nature 368 (6474):856-859 and WO 02/43478.

The antibody according to the invention may be a chimeric antibody, i.e. an antibody comprising regions derived from different species. The chimeric antibody may for example comprise variable regions from one species of animal and constant regions from another species of animal. For example, a chimeric antibody can be an antibody having variable regions which derive from a mouse monoclonal antibody and constant regions which are human. Such antibodies may also be referred to as humanized antibodies.

Thus, the antibody according to the invention may also be a humanized antibody, which is encoded partly by sequences obtained from human germline immunoglobulin sequences and partly from other sequences. Said other sequences are preferably germline immunoglobulins from other species, more preferably from other mammalian species. In particular a humanized antibody may be an antibody in which the antigen binding site is derived from an immunoglobulin from a non-human species, preferably from a non-human mammal, e.g. from a mouse or a rat, whereas some or all of the remaining immunoglobulin-derived parts of the molecule is derived from a human immunoglobulin. The antigen binding site from said non-human species may for example consist of a complete $V_L$ or $V_H$ or both or one or more CDRs grafted onto appropriate human framework regions in $V_L$ or $V_H$ or both. Thus, in a humanized antibody, the CDRs can be from a mouse or rat monoclonal antibody and the other regions of the antibody are of human origin.

By "reference antibody 'CAN03'" we include an intact IgG antibody comprising a heavy chain variable regions having the amino acid sequence of SEQ ID NO: 14; a light chain variable regions having the amino acid sequence of SEQ ID NO:15; a heavy chain constant region having the amino acid sequence of SEQ ID NO: 33, and a light chain constant region having the amino acid sequence of SEQ ID NO: 34. Alternatively, a humanised version of CAN03 may be used as the reference antibody. The reference antibody CAN03 is described in WO 2016/020502.

By "reference antibody 'CAN04'" we include an intact IgG antibody comprising a heavy chain variable region selected from the group consisting of SEQ ID NO: 4, SEQ ID NO: 5, SEQ ID NO: 6, and SEQ ID NO: 7; a light chain variable region selected from the group consisting of SEQ ID NO: 1, SEQ ID NO: 2, and SEQ ID NO: 3; a heavy chain constant region having the amino acid sequence of SEQ ID NO: 31; and a light chain constant region having the amino acid sequence of SEQ ID NO: 32. In a preferred embodiment, the heavy chain variable region is SEQ ID NO: 4, and the light chain variable region selected from the group consisting of SEQ ID NO: 1. Alternatively, a humanised version of CAN04 may be used as the reference antibody. The reference antibody CAN04 is described in WO 2015/132602.

The term "scFv" refers to single-chain Fv. A Fv fragment is a fragment wherein the variable regions of the heavy ($V_H$) and the light ($V_L$) chain are associated to form the binding site of the antibody. Flexible linkers can be used to covalently join a $V_H$ and a $V_L$ chain, forming a scFv that retains the binding specificity of the original antibody.

The term "single-chain antibodies" refers to antibodies that are single polypeptides comprising one or more antigen binding sites. Single chain antibodies may comprise the two domains of the Fv fragment, $V_L$ and $V_H$.

Binding to Extracellular Domains of IL1RAP

In one aspect, the present invention concerns a composition comprising at least a first binding agent with specificity for anti-Interleukin-1 Receptor Accessory Protein (IL1RAP) and a second binding agent with specificity for IL1RAP, wherein the first and second binding agents bind to at least two different extracellular domains of IL1RAP. For example, the first and second binding agents may bind, respectively, to the following extracellular domains od IL1RAP:
(a) domain 1 and domain 2;
(b) domain 1 and domain 3; or
(c) domain 2 and domain 3.

In one embodiment, the composition comprises binding agents that collectively bind to all three extracellular domains of IL1RAP, i.e. domains 1, 2 and 3.

By "interleukin-1 receptor accessory protein", "IL1RAP" and "IL1-RAP" we specifically include the human IL1RAP protein, for example as described in GenBank Accession NO: AAB84059, NCBI Reference Sequence: NP_002173.1 and UniProtKB/Swiss-Prot Accession NO: Q9NPH3-1 (see also Huang et al., 1997, *Proc. Natl. Acad. Sci. USA*. 94 (24), 12829-12832, the disclosures of which are incorporated herein by reference). IL1RAP is also known in the scientific literature as IL1R3, C3orf13, FLJ37788, IL-1RAcP and EG3556.

Thus, the binding agents of the invention have specificity for IL1RAP. By "specificity" we mean that the binding agents are capable of binding to IL1RAP in vivo, i.e. under the physiological conditions in which IL1RAP exists within the human body. Preferably, the binding agent does not bind to any other protein in vivo. Such binding specificity may be determined by methods well known in the art, such as ELISA, immunohistochemistry, immunoprecipitation, Western blots and flow cytometry using transfected cells expressing IL1RAP. Advantageously, the binding agent is capable of binding selectively to IL1RAP, i.e. it bind at least 10-fold more strongly to IL1RAP than to any other proteins.

The reference antibody 'CAN04' binds to domain 2 of IL1RAP (see Wang et al., 2010, *Nature Immunology*, 11:905-912, the disclosures of which are incorporated herein by reference), i.e. within amino acids 135 to 234 of IL1RAP (see Accession No. Q9NPH3 within UniProtKB/Swiss-Prot). For example, the epitope to which the antibody or antigen-binding fragment may be located within amino acids 135 to 154, 155 to 174, 175 to 194, 195 to 214 or between amino acids 215 to 234 of IL1RAP. However, it will be appreciated that the epitope may be non-linear.

In one embodiment, the antibody or antigen-binding fragment in the compositions of the invention is capable of binding to an epitope on the extracellular domain of IL1RAP which overlaps, at least in part, with the epitope on IL1RAP to which reference antibody CAN04 is capable of binding. Thus, the antibody or antigen-binding fragment may be capable of binding to an epitope located at/within domain 2 of IL1RAP.

The reference antibody 'CAN03' binds to domain 3 of IL1RAP. Thus, it will be appreciated that the antibody or an antigen-binding fragment in the compositions of the invention also binds to domain 3 of IL1RAP.

By "domain 3" of IL1RAP we include the structural region defined by amino acids 235 to 369 of IL1RAP according to numbering used in Accession No. Q9NPH3 of UniProtKB/Swiss-Prot (see also Wang et al., 2010, *Nature Immunology*, 11:905-912, the disclosures of which are incorporated herein by reference). For example, the epitope to which the antibody or antigen-binding fragment binds may be located within amino acids 235 to 239, 240 to 249, 250 to 259, 260 to 269, 270 to 279, 280 to 289, 290 to 299, 300 to 309, 310 to 319, 320 to 329, 330 to 229, 240 to 349, 350 to 359 or between amino acids 360 to 369 of IL1RAP.

The expression "capable of inhibiting the binding of reference antibody 'CAN04' (or 'CAN03') to human IL1RAP" refers to the presence of the antibody polypeptides which inhibit, in whole or in part, the binding of 'CAN04' (or 'CAN03') to human IL1RAP. An antibody capable of inhibiting the binding of antibody CAN04 (or CAN03) is to be understood as an antibody that is competing with CAN04 (or CAN03) for binding to IL1RAP. Such competitive binding inhibition can be determined using assays and methods well known in the art, for example using Surface Plasmon Resonance, or flow cytometry, or an ELISA.

Composition comprising at least two binding agents that bind to at least two different extracellular domains of IL1RAP In one embodiment, the present invention concerns a composition wherein:
a) a first binding agent is an anti-IL1RAP antibody or antigen-binding fragment thereof, selected from the group consisting of:
   i) the reference antibody "CAN04",
   ii) an antibody comprising the variable light chain ($V_L$) amino acid sequence: DIQMTQSPSSL-SASVGDRVTITCQASQGINNYLNWYQQKP GKAPKLLIHYTSGL-HAGVPSRFSGSGSGTDYTLTISSLEPED VATYYCQQYSILPWTFGGGTKVEIKR (SEQ ID NO: 1) and the variable heavy chain ($V_H$) amino acid sequence:

```
                                (SEQ ID NO: 4)
QVQLVQSGAEVKKPGSSVKVSCKASGYAFTSSWMNWVRQ

APGQGLEWMGRIYPGDGNTHYAQKFQGRVTLTADKSTSTA

YMELSSLRSEDTAVYYCGEGYLDPMDYWGQGTLVTVSS,
``` iii) an antibody comprising at least one of the following six complementary determining regions (CDRs):

```
                                    (SEQ ID NO: 8)
Light chain CDR1: SASQGINNYLN
or
                                    (SEQ ID NO: 29)
ASQGINNYLN (SEQ ID NO: 9)
Light chain CDR2: YTSGLHAGV
or
                                    (SEQ ID NO: 22)
YTSGLHA (SEQ ID NO: 10)
Light chain CDR3: QQYSILPWT
or
                                    (SEQ ID NO: 23)
QYSILPWT (SEQ ID NO: 11)
Heavy chain CDR1: GYAFTSSSWMN
or
                                    (SEQ ID NO: 24)
GYAFTSS (SEQ ID NO: 12)
Heavy chain CDR2: RIYPGDGNTHYAQKFQG
or
                                    (SEQ ID NO: 25)
YPGDGN (SEQ ID NO: 13)
Heavy chain CDR3: GYLDPMDY;
``` and
   iv) an antibody binding to the same epitope as the antibody of part (i) above,
   v) an antibody capable of inhibiting the binding of the antibody of part (i) above to human IL1RAP;
   vi) an antibody capable of binding to extracellular domain 2 of IL1RAP; and vii) an antigen-binding fragment of an antibody of (i) to (vi) above;
and
b) wherein a second binding agent is an anti-IL1RAP antibody or antigen-binding fragment thereof selected from the group consisting of:
i) the reference antibody "CAN03";
ii) an antibody comprising the variable light chain ($V_L$) amino acid sequence:

```
                                       (SEQ ID NO: 14)
DILLTQSPAILSVSPGERVSFSCRASQSIGTSIHWYQRRTNG

SPRLLIKSASESISGIPSRFSGSGSGTDFTLSINSVESEDIAD

YYCQQSNSWPTTFGAGTKLELKR,
``` and the variable heavy chain ($V_H$) amino acid sequence:

```
                                       (SEQ ID NO: 15)
DVKLVESGGGLVKPGGSLKLSCAASGFTFSIYTMSVWRQT

PEKRLEWVATISIGGSYINYPDSVKGRFTISRDNAKNTLYLQ

MSSLKSEDTAIYYCSREVDGSYAMDYWGQGTSVTVSS;
``` iii) an antibody comprising at least one of the following six complementary determining regions (CDRs):

```
                                       (SEQ ID NO: 16)
Light chain CDR1: RASQSIGTSIH
or (SEQ ID NO: 30)
ASQSIGTSIH (SEQ ID NO: 17)
Light chain CDR2: SASESIS (SEQ ID NO: 18)
Light chain CDR3: QQSNSWPTT
or (SEQ ID NO: 26)
QSNSWPTT (SEQ ID NO: 19)
Heavy chain CDR1: GFTFSIYTMS
or (SEQ ID NO: 27)
GFTFSIY (SEQ ID NO: 20)
Heavy chain CDR2: TISIGGSYINYPDSVKG
or (SEQ ID NO: 28)
SIGGSY (SEQ ID NO: 21)
Heavy chain CDR3: EVDGSYAMDY;
``` iv) an antibody binding to the same epitope as antibody of part (i) above;
v) an antibody capable of inhibiting the binding of antibody of part (i) above to human IL1RAP;
vi) an antibody capable of binding to extracellular domain 3 of IL1RAP; and
vii) an antigen-binding fragment of an antibody of (i) to (vi) above.

In one embodiment, the antibody of (a) (iii) above comprises at least one of the CDRs, such as at least two, such as at least three, such as at least four, such as at least five, such as all six of the CDRs. In another embodiment, said antibody comprises all three light chain CDRs and/or all three heavy chain CDRs.

In one embodiment, the antibody of (b) (iii) comprises at least one of the CDRs, such as at least two, such as at least three, such as at least four, such as at least five, such as all six of the CDRs. In another embodiment, said antibody comprises all three light chain CDRs and/or all three heavy chain CDRs.

In one embodiment, said first binding agent is an anti-IL1RAP antibody or antigen-binding fragment thereof comprising a variable heavy chain ($V_H$), and a variable light chain ($V_L$) selected from the group consisting of:
a) a variable heavy chain ($V_H$) comprising the amino acid sequence SEQ ID NO: 4, and a variable light chain ($V_L$) comprising the amino acid sequence SEQ ID NO: 1;
b) a variable heavy chain ($V_H$) comprising the amino acid sequence SEQ ID NO: 5, and a variable light chain ($V_L$) comprising the amino acid sequence SEQ ID NO: 1;
c) a variable heavy chain ($V_H$) comprising the amino acid sequence SEQ ID NO: 6, and a variable light chain ($V_L$) comprising the amino acid sequence SEQ ID NO: 1;
d) a variable heavy chain ($V_H$) comprising the amino acid sequence SEQ ID NO: 7, and a variable light chain ($V_L$) comprising the amino acid sequence SEQ ID NO: 1;
e) a variable heavy chain ($V_H$) comprising the amino acid sequence SEQ ID NO: 4, and a variable light chain ($V_L$) comprising the amino acid sequence SEQ ID NO: 2;
f) a variable heavy chain ($V_H$) comprising the amino acid sequence SEQ ID NO: 5, and a variable light chain ($V_L$) comprising the amino acid sequence SEQ ID NO: 2;
g) a variable heavy chain ($V_H$) comprising the amino acid sequence SEQ ID NO: 6, and a variable light chain ($V_L$) comprising the amino acid sequence SEQ ID NO: 2;
h) a variable heavy chain ($V_H$) comprising the amino acid sequence SEQ ID NO: 7, and a variable light chain ($V_L$) comprising the amino acid sequence SEQ ID NO: 2;
i) a variable heavy chain ($V_H$) comprising the amino acid sequence SEQ ID NO: 4, and a variable light chain ($V_L$) comprising the amino acid sequence SEQ ID NO: 3;
j) a variable heavy chain ($V_H$) comprising the amino acid sequence SEQ ID NO: 5, and a variable light chain ($V_L$) comprising the amino acid sequence SEQ ID NO: 3;
k) a variable heavy chain ($V_H$) comprising the amino acid sequence SEQ ID NO: 6, and a variable light chain ($V_L$) comprising the amino acid sequence SEQ ID NO: 3;
and
l) a variable heavy chain ($V_H$) comprising the amino acid sequence SEQ ID NO: 7, and a variable light chain ($V_L$) comprising the amino acid sequence SEQ ID NO: 3.

In one embodiment, said first binding agent is an anti-IL1RAP antibody or antigen-binding fragment thereof comprising:
a light chain variable domain ($V_L$) comprising or consisting of the amino acid sequence of SEQ ID NOs: 1, 2, or 3; and
a heavy chain variable domain ($V_H$) comprising or consisting of the amino acid sequence of SEQ ID NOs: 4, 5, 6, or 7; and
said second binding agent is an anti-IL1RAP antibody or antigen-binding fragment thereof comprising:
a light chain variable domain ($V_L$) comprising or consisting of the amino acid sequence of SEQ ID NO: 14; and
a heavy chain variable domain ($V_H$) comprising or consisting of the amino acids of SEQ ID NO: 15.

Preferably, said first binding agent is an anti-IL1RAP antibody or antigen-binding fragment thereof comprising a light chain variable domain ($V_L$) comprising or consisting of the amino acid sequence of SEQ ID NO: 1 and a heavy chain variable domain ($V_H$) comprising or consisting of the amino acid sequence of SEQ ID NO: 4, and said second binding agent is an anti-IL1RAP antibody or antigen-binding fragment thereof comprising a light chain variable domain ($V_L$) comprising or consisting of the amino acid sequence of SEQ ID NO: 14 and a heavy chain variable domain ($V_H$) comprising or consisting of the amino acids of SEQ ID NO: 15.

In some embodiments, said first binding agent is an anti-IL1RAP antibody or antigen-binding fragment thereof comprising a variable light chain ($V_L$) comprising or consisting of the amino acid sequence of SEQ ID NO: 1, or an amino acid sequence having at least 60% sequence identity, such as at least 70% sequence identity, such as at least 80% sequence identity, such as at least 90% sequence identity, such as at least 95% sequence identity, such as at least 97% sequence identity, such as at least 98% sequence identity, such as at least 99% sequence identity to SEQ ID NO: 1.

In some embodiments, said first binding agent is an anti-IL1RAP antibody or antigen-binding fragment thereof comprising a variable light chain ($V_L$) comprising or consisting of the amino acid sequence of SEQ ID NO: 1, or an amino acid sequence wherein any one amino acid of SEQ ID NO: 1, has been altered for another amino acid, with the proviso that no more than 3 amino acid residues have been thus altered.

In some embodiments, said first binding agent is an anti-IL1RAP antibody or antigen-binding fragment thereof comprising a variable heavy chain ($V_H$) comprising or consisting of the amino acid sequence of SEQ ID NO: 4, or an amino acid sequence having at least 60% sequence identity, such as at least 70% sequence identity, such as at least 80% sequence identity, such as at least 90% sequence identity, such as at least 95% sequence identity, such as at least 97% sequence identity, such as at least 98% sequence identity, such as at least 99% sequence identity to SEQ ID NO: 4.

In some embodiments, said first binding agent is an anti-IL1RAP antibody or antigen-binding fragment thereof comprising a variable heavy chain ($V_H$) comprising or consisting of the amino acid sequence of SEQ ID NO: 4, or an amino acid sequence wherein any one amino acid of SEQ ID NO: 4, has been altered for another amino acid, with the proviso that no more than 3 amino acid residues have been thus altered.

In some embodiments, said first binding agent is an anti-IL1RAP antibody or antigen-binding fragment thereof comprising a light chain CDR comprising or consisting of the amino acid sequence selected from the group consisting of SEQ ID NO: 8, SEQ ID NO: 9, SEQ ID NO:10, SEQ ID NO:22, SEQ ID NO: 23, and SEQ ID NO: 29, or an amino acid sequence having at least 80% sequence identity, such as at least 90% sequence identity, such as at least 95% sequence identity, such as at least 97% sequence identity, such as at least 98% sequence identity, such as at least 99% sequence identity to SEQ ID NO: 8, SEQ ID NO: 9, SEQ ID NO:10, SEQ ID NO:22, SEQ ID NO: 23, and SEQ ID NO: 29, respectively.

In some embodiments, said first binding agent is an anti-IL1RAP antibody or antigen-binding fragment thereof comprising a light chain CDR comprising or consisting of the amino acid sequence selected from the group consisting of SEQ ID NO: 8, SEQ ID NO: 9, SEQ ID NO: 10, SEQ ID NO: 22, SEQ ID NO: 23, and SEQ ID NO: 29, or an amino acid sequence wherein any one amino acid of said amino acid sequence, has been altered for another amino acid, with the proviso that no more than 3 amino acid residues have been thus altered.

In some embodiments, said first binding agent is an anti-IL1RAP antibody or antigen-binding fragment thereof comprising a heavy chain CDR comprising or consisting of the amino acid sequence selected from the group consisting of SEQ ID NO: 11, SEQ ID NO: 12, SEQ ID NO: 13, SEQ ID NO:24, and SEQ ID NO: 25, or an amino acid sequence having at least 80% sequence identity, such as at least 90% sequence identity, such as at least 95% sequence identity, such as at least 97% sequence identity, such as at least 98% sequence identity, such as at least 99% sequence identity to SEQ ID NO: 11, SEQ ID NO: 12, SEQ ID NO: 13, SEQ ID NO:24, and SEQ ID NO: 25, respectively.

In some embodiments, said first binding agent is an anti-IL1RAP antibody or antigen-binding fragment thereof comprising a light chain CDR comprising or consisting of the amino acid sequence selected from the group consisting of SEQ ID NO: 11, SEQ ID NO: 12, SEQ ID NO: 13, SEQ ID NO: 24, and SEQ ID NO: 25, or an amino acid sequence wherein any one amino acid of said amino acid sequence, has been altered for another amino acid, with the proviso that no more than 3 amino acid residues have been thus altered.

In some embodiments, said second binding agent is an anti-IL1RAP antibody or antigen-binding fragment thereof comprising a variable light chain ($V_L$) comprising or consisting of the amino acid sequence of SEQ ID NO: 14, or an amino acid sequence having at least 80% sequence identity, such as at least 90% sequence identity, such as at least 95% sequence identity, such as at least 97% sequence identity, such as at least 98% sequence identity, such as at least 99% sequence identity to SEQ ID NO: 14.

In some embodiments, said second binding agent is an anti-IL1RAP antibody or antigen-binding fragment thereof comprising a variable light chain ($V_L$) comprising or consisting of the amino acid sequence of SEQ ID NO: 14, or an amino acid sequence wherein any one amino acid of SEQ ID NO: 14, has been altered for another amino acid, with the proviso that no more than 3 amino acid residues have been thus altered.

In some embodiments, said second binding agent is an anti-IL1RAP antibody or antigen-binding fragment thereof comprising a variable heavy chain ($V_H$) comprising or consisting of the amino acid sequence of SEQ ID NO: 15, or an amino acid sequence having at least 80% sequence identity, such as at least 90% sequence identity, such as at least 95% sequence identity, such as at least 97% sequence identity, such as at least 98% sequence identity, such as at least 99% sequence identity to SEQ ID NO: 15.

In some embodiments, said second binding agent is an anti-IL1RAP antibody or antigen-binding fragment thereof comprising a variable heavy chain ($V_H$) comprising or consisting of the amino acid sequence of SEQ ID NO: 15, or an amino acid sequence wherein any one amino acid of SEQ ID NO: 15, has been altered for another amino acid, with the proviso that no more than 3 amino acid residues have been thus altered.

In some embodiments, said second binding agent is an anti-IL1RAP antibody or antigen-binding fragment thereof comprising a light chain CDR comprising or consisting of the amino acid sequence selected from the group consisting of SEQ ID NO: 16, SEQ ID NO: 17, SEQ ID NO: 18, SEQ ID NO: 26, and SEQ ID NO: 30, or an amino acid sequence having at least 80% sequence identity, such as at least 90% sequence identity, such as at least 95% sequence identity, such as at least 97% sequence identity, such as at least 98% sequence identity, such as at least 99% sequence identity to SEQ ID NO: 16, SEQ ID NO: 17, SEQ ID NO: 18, SEQ ID NO: 26, and SEQ ID NO: 30, respectively.

In some embodiments, said second binding agent is an anti-IL1RAP antibody or antigen-binding fragment thereof comprising a light chain CDR comprising or consisting of the amino acid sequence selected from the group consisting of SEQ ID NO: 16, SEQ ID NO: 17, SEQ ID NO: 18, SEQ ID NO: 26, and SEQ ID NO: 30, or an amino acid sequence wherein any one amino acid of said amino acid sequence, has been altered for another amino acid, with the proviso that no more than 3 amino acid residues have been thus altered.

In some embodiments, said second binding agent is an anti-IL1RAP antibody or antigen-binding fragment thereof comprising a heavy chain CDR comprising or consisting of the amino acid sequence selected from the group consisting of SEQ ID NO: 19, SEQ ID NO: 20, SEQ ID NO: 21, SEQ ID NO: 27, and SEQ ID NO: 28, or an amino acid sequence having at least 80% sequence identity, such as at least 90% sequence identity, such as at least 95% sequence identity, such as at least 97% sequence identity, such as at least 98% sequence identity, such as at least 99% sequence identity to SEQ ID NO: 19, SEQ ID NO: 20, SEQ ID NO:21, SEQ ID NO: 27, and SEQ ID NO: 28, respectively.

In some embodiments, said second binding agent is an anti-IL1RAP antibody or antigen-binding fragment thereof comprising a heavy chain CDR comprising or consisting of the amino acid sequence selected from the group consisting of SEQ ID NO: 19, SEQ ID NO: 20, SEQ ID NO: 21, SEQ ID NO: 27, and SEQ ID NO: 28, or an amino acid sequence wherein any one amino acid of said amino acid sequence, has been altered for another amino acid, with the proviso that no more than 3 amino acid residues have been thus altered.

In some embodiments, the proportion of said first binding agent relative to said second binding agent in said composition is between 10:1 and 1:10, such as between 5:1 and 1:5, such as between 2:1 and 1:2, such as between 3:2 and 2:3, such as between 11:9 and 9:11, such as 1:1.

In some embodiments, said first and second binding agents are antibody molecules of isotype subtype IgG1, IgG2, IgG3 or IgG4.

In some embodiments, said composition is capable of inducing internalisation of cell membrane-bound IL1RAP. By internalisation, we mean that upon binding of the binding agents within the compositions of the invention to IL1RAP located within the membrane of a cell, the binding agent-IL1RAP complex is internalised within the cell.

In some embodiments, said first and/or second binding agent(s) lack the capacity to induce antibody dependent cell mediated cytotoxicity (ADCC).

Bi-Epitopic Binding Agents that Bind to at Least Two Different Extracellular Domains of IL1RAP In one aspect, the present invention concerns a bi-epitopic binding agent comprising:
a first antigen-binding region, and
a second antigen-binding region,
wherein the first distinct antigen binding region and the second distinct antigen binding region bind to two different extracellular domains of human interleukin-receptor accessory protein (IL1RAP).

A "bi-epitopic binding agent" as used herein refers to a molecule capable of binding to two different epitopes simultaneously. A bi-epitopic binding agent may be a bispecific agent. A "bispecific agent" as used herein refers to a molecule capable of binding to two different epitopes on two different molecules.

In some embodiments, said bi-epitopic binding agent is a dual-variable-domain antibody, a bi-epitopic Fab-fragment, a bi-epitopic scFv, a bivalent bispecific antibody (such as IgG-scFv bispecific antibodies), a monovalent bispecific antibody (such as a DuoBody®, Genmab AS, Copenhagen, Denmark), a 'knob-in-hole' bispecific antibody (for example, an scFv-KIH, scFv-KIHr, a BITE-KIH or a BITE-KIHr; see Xu et al., 2015, mAbs 7 (1):231-242), a scFv2-Fc bispecific antibody, a BiTE/scFv2 bispecific antibody, a DVD-Ig bispecific antibody, an IgG-Fab bispecific antibody, a FAb-IgG bispecific antibody, a DART-based bispecific antibody (such as DART2-Fc, DART2-Fc or DART), a DNL-Fab3 bispecific antibody, or a scFv-HSA-scFv bispecific antibody.

In one embodiment, said bi-epitopic binding agent is a polypeptide, such as an antibody.

In one embodiment, the present invention concerns said bi-epitopic binding agent wherein:
a) the first antigen-binding region is selected from the group consisting of:
i) an antigen-binding region which binds to the same antigen as the reference antibody "CAN04";
ii) an antigen-binding region which binds to the same epitope as the antibody CAN04;
iii) an antigen-binding region which is capable of inhibiting the binding of the antibody CAN04 to human IL1RAP;
iv) an antigen-binding region which is capable of binding to domain 2 of IL1RAP;
v) an amino acid sequence comprising or consisting of: the variable light chain (V$_L$) amino acid sequence: DIQMTQSPSSLSASVGDRVTITCQASQGIN-NYLNWYQQKP GKAPKLLIHYTSGL-HAGVPSRFSGSGSGTDYTLTISSLEPED VATYYCQQYSILPWTFGGGTKVEIKR (SEQ ID NO:1) and the variable heavy chain (V$_H$) amino acid sequence: DVKLVESGGGLVKPGGSLKLS-CAASGFTFSIYTMSWVRQT PEKRLEWVA-TISIGGSYINYPDSVKGRFTISRDNAKNTLYLQ MSSLKSEDTAIYYCS-REVDGSYAMDYWGQGTSVTVSS (SEQ ID NO:4) of the antibody CAN04,
vi) an amino acid sequence comprising or consisting of at least one of the following six complementary determining regions (CDRs):

```
                                      (SEQ ID NO: 8)
Light chain CDR1: SASQGINNYLN
or
                                      (SEQ ID NO: 29)
ASQGINNYLN (SEQ ID NO: 9)
Light chain CDR2: YTSGLHAGV
or
                                      (SEQ ID NO: 22)
YTSGLHA (SEQ ID NO: 10)
Light chain CDR3: QQYSILPWT
or
                                      (SEQ ID NO: 23)
QYSILPWT
```

```
                                                    (SEQ ID NO: 11)
Heavy chain CDR1: GYAFTSSSWMN
or (SEQ ID NO: 24)
GYAFTSS (SEQ ID NO: 12)
Heavy chain CDR2: RIYPGDGNTHYAQKFQG
or (SEQ ID NO: 25)
YPGDGN (SEQ ID NO: 13)
Heavy chain CDR3: GYLDPMDY;
``` vii) an antigen-binding fragment of an antibody of (i) to (vi) above;

and b) the second antigen-binding region is selected from the group consisting of:
  i) an antigen-binding region which binds to the same antigen as the reference antibody "CAN03";
  ii) an antigen-binding region which binds to the same epitope as the antibody CAN03;
  iii) an antigen-binding region which is capable of inhibiting the binding of the antibody CAN03 to human IL1RAP;
  iv) an antigen-binding region which is capable of binding to the extracellular domain 3 of IL1RAP;
  v) an amino acid sequence comprising or consisting of the variable light chain ($V_L$) amino acid sequence:

```
                                                    (SEQ ID NO: 14)
DILLTQSPAILSVSPGERVSFSCRASQSIGTSIHWYQRRTNG

SPRLLIKSASESISGIPSRFSGSGSGTDFTLSINSVESEDIAD

YYCQQSNSWPTTFGAGTKLELKR,
``` and the variable heavy chain ($V_H$) amino acid sequence: DVKLVESGGGLVKPGGSLKLS-CAASGFTFSIYTMSWVRQT PEKRLEWVA-TISIGGSYINYPDSVKGRFTISRDNAKNTLYLQ MSSLKSEDTAIYYCS-REVDGSYAMDYWGQGTSVTVSS (SEQ ID NO: 15) of the antibody CAN03,
  vi) an antigen binding region comprising at least one of the following six complementary determining regions (CDRs):

```
                                                    (SEQ ID NO: 16)
Light chain CDR1: RASQSIGTSIH
or (SEQ ID NO: 30)
ASQSIGTSIH (SEQ ID NO: 17)
Light chain CDR2: SASESIS (SEQ ID NO: 18)
Light chain CDR3: QQSNSWPTT
or (SEQ ID NO: 26)
QSNSWPTT
```

```
                                                    (SEQ ID NO: 19)
Heavy chain CDR1: GFTFSIYTMS
or (SEQ ID NO: 27)
GFTFSIY (SEQ ID NO: 20)
Heavy chain CDR2: TISIGGSYINYPDSVKG
or (SEQ ID NO: 28)
SIGGSY (SEQ ID NO: 21)
Heavy chain CDR3: EVDGSYAMDY;
``` and vii) an antigen-binding fragment of an antibody of (i) to (vi) above.

In one embodiment, said first antigen-binding region comprises an amino acid sequence comprising or consisting of the heavy chain amino acid sequence SEQ ID NO: 35 and the light chain amino acid sequence SEQ ID NO: 36 and wherein said second antigen-binding region comprises the heavy chain amino acid sequence SEQ ID NO: 37 and the light chain amino acid sequence SEQ ID NO: 38.

In one embodiment, said first antigen binding region comprises a variable heavy chain ($V_H$), and a variable light chain ($V_L$) selected from the group consisting of:
  a) a variable heavy chain ($V_H$) comprising the amino acid sequence SEQ ID NO: 4, and a variable light chain ($V_L$) comprising the amino acid sequence SEQ ID NO: 1;
  b) a variable heavy chain ($V_H$) comprising the amino acid sequence SEQ ID NO: 5, and a variable light chain ($V_L$) comprising the amino acid sequence SEQ ID NO: 1;
  c) a variable heavy chain ($V_H$) comprising the amino acid sequence SEQ ID NO: 6, and a variable light chain ($V_L$) comprising the amino acid sequence SEQ ID NO: 1;
  d) a variable heavy chain ($V_H$) comprising the amino acid sequence SEQ ID NO: 7, and a variable light chain ($V_L$) comprising the amino acid sequence SEQ ID NO: 1;
  e) a variable heavy chain ($V_H$) comprising the amino acid sequence SEQ ID NO: 4, and a variable light chain ($V_L$) comprising the amino acid sequence SEQ ID NO: 2;
  f) a variable heavy chain ($V_H$) comprising the amino acid sequence SEQ ID NO: 5, and a variable light chain ($V_L$) comprising the amino acid sequence SEQ ID NO: 2;
  g) a variable heavy chain ($V_H$) comprising the amino acid sequence SEQ ID NO: 6, and a variable light chain ($V_L$) comprising the amino acid sequence SEQ ID NO: 2;
  h) a variable heavy chain ($V_H$) comprising the amino acid sequence SEQ ID NO: 7, and a variable light chain ($V_L$) comprising the amino acid sequence SEQ ID NO: 2;
  i) a variable heavy chain ($V_H$) comprising the amino acid sequence SEQ ID NO: 4, and a variable light chain ($V_L$) comprising the amino acid sequence SEQ ID NO: 3;
  j) a variable heavy chain ($V_H$) comprising the amino acid sequence SEQ ID NO: 5, and a variable light chain ($V_L$) comprising the amino acid sequence SEQ ID NO: 3;
  k) a variable heavy chain ($V_H$) comprising the amino acid sequence SEQ ID NO: 6, and a variable light chain ($V_L$) comprising the amino acid sequence SEQ ID NO: 3;

and l) a variable heavy chain ($V_H$) comprising the amino acid sequence SEQ ID NO: 7, and a variable light chain ($V_L$) comprising the amino acid sequence SEQ ID NO: 3.

In one embodiment, said first antigen-binding region comprises a light chain variable domain ($V_L$) comprising or consisting of the amino acid sequence of SEQ ID NOs: 1, 2, or 3; and a heavy chain variable domain ($V_H$) comprising or consisting of the amino acid sequence of SEQ ID NOs: 4, 5, 6, or 7; and said second antigen binding-region comprises a light chain variable domain ($V_L$) comprising or consisting of the amino acid sequence of SEQ ID NO: 14; and a heavy chain variable domain ($V_H$) comprising or consisting of the amino acids of SEQ ID NO: 15.

Preferably, said first antigen-binding region comprises a light chain variable domain ($V_L$) comprising or consisting of the amino acid sequence of SEQ ID NO: 1; and a heavy chain variable domain ($V_H$) comprising or consisting of the amino acid sequence of SEQ ID NO: 4; and said second antigen-binding region comprises a light chain variable domain ($V_L$) comprising or consisting of the amino acid sequence of SEQ ID NO: 14; and a heavy chain variable domain ($V_H$) comprising or consisting of the amino acid sequence of SEQ ID NO: 15.

In some embodiments, said first antigen-binding region has a variable light chain ($V_L$) comprising or consisting of the amino acid sequence of SEQ ID NO: 1, or an amino acid sequence having at least 60% sequence identity, such as at least 70% sequence identity, such as at least 80% sequence identity, such as at least 90% sequence identity, such as at least 95% sequence identity, such as at least 97% sequence identity, such as at least 98% sequence identity, such as at least 99% sequence identity to SEQ ID NO: 1.

In some embodiments, said first antigen-binding region has a variable light chain ($V_L$) comprising or consisting of the amino acid sequence of SEQ ID NO: 1, or an amino acid sequence wherein any one amino acid of SEQ ID NO: 1, has been altered for another amino acid, with the proviso that no more than 3 amino acid residues have been thus altered.

In some embodiments, said first antigen-binding region has a variable heavy chain ($V_H$) comprising or consisting of the amino acid sequence of SEQ ID NO: 4, or an amino acid sequence having at least 60% sequence identity, such as at least 70% sequence identity, such as at least 80% sequence identity, such as at least 90% sequence identity, such as at least 95% sequence identity, such as at least 97% sequence identity, such as at least 98% sequence identity, such as at least 99% sequence identity to SEQ ID NO: 4.

In some embodiments, said first antigen-binding region has a variable heavy chain ($V_H$) comprising or consisting of the amino acid sequence of SEQ ID NO: 4, or an amino acid sequence wherein any one amino acid of SEQ ID NO: 4, has been altered for another amino acid, with the proviso that no more than 3 amino acid residues have been thus altered.

In some embodiments, said first antigen-binding region has a light chain CDR comprising or consisting of the amino acid sequence selected from the group consisting of SEQ ID NO: 8, SEQ ID NO: 9, SEQ ID NO: 10, SEQ ID NO:22, SEQ ID NO: 23, and SEQ ID NO: 29, or an amino acid sequence having at least 80% sequence identity, such as at least 90% sequence identity, such as at least 95% sequence identity, such as at least 97% sequence identity, such as at least 98% sequence identity, such as at least 99% sequence identity to SEQ ID NO: 8, SEQ ID NO: 9, SEQ ID NO: 10, SEQ ID NO:22, SEQ ID NO: 23, and SEQ ID NO: 29, respectively.

In some embodiments, said first antigen-binding region has a light chain CDR comprising or consisting of the amino acid sequence selected from the group consisting of SEQ ID NO: 8, SEQ ID NO: 9, SEQ ID NO: 10, SEQ ID NO: 22, SEQ ID NO: 23, and SEQ ID NO: 29, or an amino acid sequence wherein any one amino acid of said amino acid sequence, has been altered for another amino acid, with the proviso that no more than 3 amino acid residues have been thus altered.

In some embodiments, said first anti-IL1RAP antibody has a heavy chain CDR comprising or consisting of the amino acid sequence selected from the group consisting of SEQ ID NO: 11, SEQ ID NO: 12, SEQ ID NO: 13, SEQ ID NO:24, and SEQ ID NO: 25, or an amino acid sequence having at least 80% sequence identity, such as at least 90% sequence identity, such as at least 95% sequence identity, such as at least 97% sequence identity, such as at least 98% sequence identity, such as at least 99% sequence identity to SEQ ID NO: 11, SEQ ID NO: 12, SEQ ID NO:13, SEQ ID NO:24, and SEQ ID NO: 25, respectively.

In some embodiments, said first antigen-binding region has a light chain CDR comprising or consisting of the amino acid sequence selected from the group consisting of SEQ ID NO: 11, SEQ ID NO: 12, SEQ ID NO: 13, SEQ ID NO: 24, and SEQ ID NO: 25, or an amino acid sequence wherein any one amino acid of said amino acid sequence, has been altered for another amino acid, with the proviso that no more than 3 amino acid residues have been thus altered.

In some embodiments, said second antigen-binding region has a variable light chain ($V_L$) comprising or consisting of the amino acid sequence of SEQ ID NO: 14, or an amino acid sequence having at least 80% sequence identity, such as at least 90% sequence identity, such as at least 95% sequence identity, such as at least 97% sequence identity, such as at least 98% sequence identity, such as at least 99% sequence identity to SEQ ID NO: 14.

In some embodiments, said second antigen-binding region has a variable light chain ($V_L$) comprising or consisting of the amino acid sequence of SEQ ID NO: 14, or an amino acid sequence wherein any one amino acid of SEQ ID NO: 14, has been altered for another amino acid, with the proviso that no more than 3 amino acid residues have been thus altered.

In some embodiments, said second antigen-binding region has a variable heavy chain ($V_H$) comprising or consisting of the amino acid sequence of SEQ ID NO: 15, or an amino acid sequence having at least 80% sequence identity, such as at least 90% sequence identity, such as at least 95% sequence identity, such as at least 97% sequence identity, such as at least 98% sequence identity, such as at least 99% sequence identity to SEQ ID NO: 15.

In some embodiments, said second antigen-binding region has a variable heavy chain ($V_H$) comprising or consisting of the amino acid sequence of SEQ ID NO: 15, or an amino acid sequence wherein any one amino acid of SEQ ID NO: 15, has been altered for another amino acid, with the proviso that no more than 3 amino acid residues have been thus altered.

In some embodiments, said second antigen-binding region has a light chain CDR comprising or consisting of the amino acid sequence selected from the group consisting of SEQ ID NO: 16, SEQ ID NO: 17, SEQ ID NO: 18, SEQ ID NO: 26, and SEQ ID NO: 30, or an amino acid sequence having at least 80% sequence identity, such as at least 90% sequence identity, such as at least 95% sequence identity, such as at least 97% sequence identity, such as at least 98% sequence identity, such as at least 99% sequence identity to SEQ ID NO: 16, SEQ ID NO: 17, SEQ ID NO: 18, SEQ ID NO: 26, and SEQ ID NO: 30, respectively.

In some embodiments, said second antigen-binding region has a light chain CDR comprising or consisting of the amino acid sequence selected from the group consisting of SEQ ID NO: 16, SEQ ID NO: 17, SEQ ID NO: 18, SEQ ID NO: 26, and SEQ ID NO: 30, or an amino acid sequence wherein any one amino acid of said amino acid sequence, has been altered for another amino acid, with the proviso that no more than 3 amino acid residues have been thus altered.

In some embodiments, said second antigen-binding region has a heavy chain CDR comprising or consisting of the amino acid sequence selected from the group consisting of SEQ ID NO: 19, SEQ ID NO: 20, SEQ ID NO: 21, SEQ ID NO: 27, and SEQ ID NO: 28, or an amino acid sequence having at least 80% sequence identity, such as at least 90% sequence identity, such as at least 95% sequence identity, such as at least 97% sequence identity, such as at least 98% sequence identity, such as at least 99% sequence identity to SEQ ID NO: 19, SEQ ID NO: 20, SEQ ID NO:21, SEQ ID NO: 27, and SEQ ID NO: 28, respectively.

In some embodiments, said second antigen-binding region has a heavy chain CDR comprising or consisting of the amino acid sequence selected from the group consisting of SEQ ID NO: 19, SEQ ID NO: 20, SEQ ID NO: 21, SEQ ID NO: 27, and SEQ ID NO: 28, or an amino acid sequence wherein any one amino acid of said amino acid sequence, has been altered for another amino acid, with the proviso that no more than 3 amino acid residues have been thus altered.

In one embodiment, the said bi-epitopic binding agent has a binding affinity ($K_D$) for human IL1RAP of 200 pM or greater.

Polynucleotides, Vectors and Host Cells

In one aspect, the present invention concerns a composition comprising one or more polynucleotides, which, collectively or individually, encode either (i) first and second binding agents or (ii) a bi-epitopic binding agent as defined herein. In another aspect, the present invention concerns an isolated polynucleotide encoding either (i) first and second binding agents or (ii) a bi-epitopic binding agent as defined herein. In yet another aspect, the present invention concerns an expression vector comprising one or more polynucleotides which, collectively or individually, encode either (i) first and second binding agents or (ii) a bi-epitopic binding agent as defined herein. In yet another aspect, the current invention concerns a host cell comprising one or more polynucleotides which, collectively or individually, encode either (i) first and second binding agents or (ii) a bi-epitopic antibody as defined herein. In yet another aspect, the current invention concerns a host cell comprising one or more expression vectors as described herein.

Pharmaceutical Compositions

Whilst it is possible for the binding agents or salts of the present invention to be administered as the raw compounds as described above, it is preferred to present them in the form of a pharmaceutical formulation. Accordingly, the present invention further provides a pharmaceutical formulation, which comprises the binding agents of the present invention or a pharmaceutically acceptable salt or ester thereof, as herein defined, and a pharmaceutically acceptable carrier therefor. The pharmaceutical formulations may be prepared by conventional techniques, e.g. as described in Remington: The Science and Practice of Pharmacy 2005, Lippincott, Williams & Wilkins.

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for parenteral, e.g. intravenous, intramuscular or subcutaneous administration (e.g., by injection or infusion). Depending on the route of administration, the binding agents may be coated in a material to protect the polypeptide from the action of acids and other natural conditions that may inactivate or denature the polypeptide.

Optional pharmaceutically acceptable carriers comprise aqueous carriers or diluents. Examples of suitable aqueous carriers that may be employed in the compositions of the invention include water, buffered water and saline. Examples of other carriers include ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants. In many cases, it will be preferable to include isotonic agents, for example, sugars, polyalcohols such as mannitol, sorbitol, or sodium chloride in the composition.

A composition of the invention also may include a pharmaceutically acceptable anti-oxidant. These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminium monostearate and gelatin.

Therapeutic compositions typically must be sterile and stable under the conditions of manufacture and storage. The composition can be formulated as a solution, microemulsion, liposome, or other ordered structure suitable to high drug concentration.

Sterile injectable solutions can be prepared by incorporating the active agent (e.g. antibody) in the required amount in an appropriate solvent with one or a combination of ingredients enumerated above, as required, followed by sterilization microfiltration. Generally, dispersions are prepared by incorporating the active agent into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active agent plus any additional desired ingredient from a previously sterile-filtered solution thereof.

In one embodiment, the compositions are formulated for systemic administration or for local administration. Local administration may be at the site of a tumour or into a tumour draining lymph node. The composition may optionally be formulated for sustained release over a period of time. Thus, the composition may be provided in or as part of a matrix facilitating sustained release. Exemplary sustained release matrices may comprise a montanide or γ-polyglutamic acid (PGA) nanoparticles.

It will be appreciated by persons skilled in the art that the compositions of the invention may comprise additional active ingredients, as well as one or more agents of the invention.

Routes of Administration and Dosages

The pharmaceutical compositions according to the invention may be administered via any suitable route known to those skilled in the art. Thus, possible routes of administration include parenteral (intravenous, subcutaneous, and intramuscular), topical, ocular, nasal, pulmonar, buccal, oral, parenteral, vaginal and rectal. Also administration from implants is possible.

As detailed above, the pharmaceutical compositions of the invention may be formulated for systemic administration or for local administration. Local administration may be at the site of a tumour or into a tumour draining lymph node. In one embodiment, the composition is formulated for sustained release over a period of time (for example, over 1 hour or more, e.g. over two, three, four, five, six, twelve, or twenty-four hours or more). The binding agents and compositions of the invention may be used in therapy or prophylaxis. In therapeutic applications, binding agents and compositions are administered to a subject already suffering from a disorder or condition, in an amount sufficient to cure, alleviate or partially arrest the condition or one or more of its symptoms. Such therapeutic treatment may result in a decrease in severity of disease symptoms, or an increase in frequency or duration of symptom-free periods. An amount adequate to accomplish this is defined as "therapeutically effective amount". In prophylactic applications, binding agents and compositions are administered to a subject not yet exhibiting symptoms of a disorder or condition, in an amount sufficient to prevent or delay the development of symptoms. Such an amount is defined as a "prophylactically effective amount". The subject may have been identified as being at risk of developing the disease or condition by any suitable means.

A suitable dosage of a binding agent or composition of the invention may be determined by a skilled medical practitioner. Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular agent employed, the route of administration, the time of administration, the rate of excretion of the polypeptide, the duration of the treatment, other drugs, compounds and/or materials used in combination with the particular compositions employed, the age, sex, weight, condition, general health and prior medical history of the patient being treated, and like factors well known in the medical arts.

Dosage regimens may be adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier.

The binding agents and compositions may be administered in a single dose or in multiple doses. The multiple doses may be administered via the same or different routes and to the same or different locations. Alternatively, a binding agent or composition can be administered as a sustained release formulation as described above, in which case less frequent administration is required. Dosage and frequency may vary depending on the half-life of the polypeptide in the patient and the duration of treatment that is desired. The dosage and frequency of administration can also vary depending on whether the treatment is prophylactic or therapeutic. In prophylactic applications, a relatively low dosage may be administered at relatively infrequent intervals over a long period of time. In therapeutic applications, a relatively high dosage may be administered, for example until the patient shows partial or complete amelioration of symptoms of disease.

Combined administration of two or more agents may be achieved in a number of different ways. In one embodiment, the first binding agent and the other agent(s) may be administered together in a single composition. In another embodiment, the first binding agent and the other agent(s) may be administered in separate compositions as part of a combined therapy.

Methods for Treatment, Amelioration, Prevention, Diagnosis or Prognosis

In one aspect, the current invention concerns a composition comprising at least two binding agents; or a bi-epitopic binding agent; or a polynucleotide; or a vector; or a host cell; or a pharmaceutical composition as described herein for use as a medicament.

In one aspect, the current invention concerns a composition comprising at least two binding agents; or a bi-epitopic binding agent; or a polynucleotide; or a vector; or a host cell; or a pharmaceutical composition as described herein for use as a diagnostic and/or prognostic agent.

In one aspect, the current invention concerns a composition comprising at least two binding agents; or a bi-epitopic binding agent; or a polynucleotide; or a vector; or a host cell; or a pharmaceutical composition as described herein for use in the treatment, amelioration, prevention, diagnosis or prognosis of an IL1RAP-associated disease or disorder in a mammal. In some embodiments, said IL1RAP-associated disease or disorder is selected from the group consisting of proliferative disorders, autoimmune disorders, and inflammatory disorders, such as auto inflammatory disorders.

In one embodiment, the current invention concerns a composition comprising at least two binding agents; or a bi-epitopic binding agent; or a polynucleotide; or a vector; or a host cell; or a pharmaceutical composition as described herein for use in the treatment, amelioration, prevention, diagnosis or prognosis of a disease or disorder selected from the group consisting of rheumatoid arthritis, osteoarthritis, multiple sclerosis, artherosclerosis, scleroderma (systemic sclerosis), lupus, systemic lupus erythematosus (SLE), (acute) glomerulonephritis, asthma, chronic obstructive pulmonary diseases (COPD), respiratory distress-syndrome (ARDS), inflammatory bowel disease, colitis, vasculitis, uveitis, dermatitis, atopic dermatitis, alopecia, rhinitis (allergica), allergic conjunctivitis, myasthenia gravis, sclerodermitis, sarcoidosis, psoriatic arthritis, psoriasis, ankylosing-spondylitis, juvenile idiopathic arthritis, Graves' disease, Sjogren's syndrome, endometriosis, Crohns disease, Behçet disease, celiac disease, diabetes mellitus type 1, Graves' disease, inflammatory bowel disease, multiple sclerosis, psoriasis, rheumatoid arthritis, systemic lupus erythematosus, familial Mediterranean fever (FMF), hyperimmunoglobulinemia D with recurrent fever (HIDS), TNF receptor-associated periodic syndrome (TRAPS), cryopyrin-associated periodic syndromes (CAPS, such as Muckle-Wells syndrome, familial cold urticaria, and neonatal onset), multisystem inflammatory disease (NOMID), periodic fever, aphthous stomatitis, pharyngitis and adenitis (PFAPA syndrome), Blau syndrome, pyogenic sterile arthritis, pyoderma gangrenosum, acne (PAPA), deficiency of the interleukin-1-receptor antagonist (DIRA), adult-onset Still's disease and systemic-onset juvenile idiopathic arthritis.

In one aspect, the current invention concerns a first binding agent with specificity for IL1RAP as defined in herein for use in the treatment, amelioration, prevention, diagnosis or prognosis of an IL1RAP-associated disease or disorder in a mammal, wherein the first binding agent is for use in combination with one or more further binding agents with specificity for IL1RAP, wherein the first and further binding agents bind to at least two different extracellular domains of IL1RAP.

Inflammatory Diseases and Disorders

In one embodiment, said IL1RAP-associated disease or disorder is an inflammatory disease or disorder.

In one embodiment, said inflammatory disease or disorder is selected from the group consisting of rheumatoid arthritis, osteoarthritis, multiple sclerosis, artherosclerosis, scleroderma (systemic sclerosis), lupus, systemic lupus erythematosus (SLE), (acute) glomerulonephritis, asthma, chronic obstructive pulmonary diseases (COPD), respiratory distress-syndrome (ARDS), inflammatory bowel disease, colitis, vasculitis, uveitis, dermatitis, atopic dermatitis, alopecia, rhinitis (allergica), allergic conjunctivitis, myasthenia gravis, sclerodermitis, sarcoidosis, psoriatic arthritis, psoriasis, ankylosingspondylitis, juvenile idiopathic arthritis, Graves disease, Sjogren's syndrome, Endometriosis, Crohns disease and Behçet disease.

Autoimmune Diseases and Disorders

In one embodiment, said IL1RAP-associated disease or disorder is an autoimmune disease or disorder.

In one embodiment, said autoimmune disease is selected from the group consisting of celiac disease, diabetes mellitus type 1, Graves disease, inflammatory bowel disease, multiple sclerosis, psoriasis, rheumatoid arthritis, and systemic lupus erythematosus.

Autoinflammatory Diseases and Disorders

In one embodiment, said IL1RAP-associated disease or disorder is an autoinflammatory disease or disorder.

In one embodiment, said autoinflammatory disease or disorder is selected from the group consisting of Familial Mediterranean Fever (FMF), Hyperimmunoglobulinemia D with recurrent fever (HIDS), TNF receptor associated periodic syndrome (TRAPS), cryopyrin-associated periodic syndromes (CAPS, such as Muckle-Wells syndrome, familial cold urticaria, and neonatal onset), multisystem inflammatory disease (NOMID), Periodic fever, aphthous stomatitis, pharyngitis and adenitis (PFAPA syndrome), Blau syndrome, Pyogenic sterile arthritis, pyoderma gangrenosum, acne (PAPA), Deficiency of the interleukin-1-receptor antagonist (DIRA), adult-onset Still's disease and systemic-onset juvenile idiopathic arthritis.

Neoplastic Disorders

In one embodiment, said IL1RAP-associated disease or disorder is a neoplastic disorder in a mammal.

In one embodiment, said neoplastic disorder is selected from the group consisting of prostate cancer, breast cancer, lung cancer, colorectal cancer, melanomas, bladder cancer, brain/CNS cancer, cervical cancer, oesophageal cancer, gastric cancer, head/neck cancer, kidney cancer, liver cancer, lymphomas, ovarian cancer, pancreatic cancer, sarcomas, chronic myeloid leukemia (CML), myeloproliferative disorders (MPD), myelodysplastic syndrome (MDS), acute lymphoblastic leukemia (ALL) and acute myeloid leukemia (AML).

Examples

A. Binding Affinity of Exemplary Antibodies for IL1RAP Protein (i) Biacore Study-Anti-IL1RAP Antibodies of Murine Origin Materials & Methods Goat anti-mouse IgG was immobilized on a CM5 chip according to the technical manual of capture kit and standard operation principle of BIAcore T200 (Biacore Life Sciences, GE Healthcare Europe GmbH, Uppsala, Sweden).

The binding analysis cycle consisted of three steps: (i) capture of the ligand on the chip surface by immobilized anti-mouse antibody; (ii) binding of the analyte to the captured ligand; and (iii) dissociation of bound analyte.

The capture molecule surface was regenerated after each binding cycle using the manufacturer's recommended conditions.

All binding cycles were run at 25° C.

After five cycles of start-up, each antibody (100 nM) was injected at a flow rate of 30 µl/min, for 120 s, at the start of the cycle; then the analyte (100 nM) was injected at a flow rate of 30 µl/min, for 120 s, followed by monitoring the dissociation phase for 300 s.

The exemplary antibodies of the compositions of the invention (CAN03 and CAN04) were tested along with one comparator anti-IL1RAP antibody (CAN01).

Results & Conclusions

Results are shown in Table 2 below:

TABLE 2

| Measurement of $K_{on}$, $K_{off}$ and $K_D$. | | | |
|---|---|---|---|
| Antibody | ka (1/M · s) | kd (1/s) | KD (M) |
| CAN01 | 2.34E+05 | 3.35E−04 | 1.43E−09 |
| CAN03 | 2.26E+05 | 7.25E−05 | 3.21E−10 |
| CAN04 | 4.27E+05 | 4.72E−05 | 1.10E−10 |

The exemplary antibodies of the invention, CAN03 and CAN04, exhibited a high affinity for human IL1RAP.

(ii) ELISA Study-Anti-IL1RAP Antibodies of Murine Origin

Materials & Methods

An indirect ELISA assay was performed. All samples were analysed in duplicate. Nunc-MaxiSorp 96 Micro Well™ Plates were coated with 100 ng of recombinant hIL1RAP 21-367 (100 µl/well) diluted in 0.01M PBS, pH 7.4, and incubated overnight at 4° C. Plates were washed with ELISA washing buffer (0.01M PBS, 0.05% Tween 20, pH 7.4) followed by a blocking step using 150 µl/well of ELISA blocking solution (PBS, 0.5% BSA, 0.05% Tween 20, pH 7.4). After 1 h incubation at room temperature (RT) on agitation the plates were washed again using ELISA washing buffer. Samples were diluted in three-fold serial dilution (ranging from 1000 ng/ml to 0.5 ng/ml) in ELISA blocking solution and then transferred to the ELISA plate, 100 µl/well. Plates were incubated at RT for 1 h on agitation and then washed with ELISA washing solution. 100 µl/well of rabbit anti-mouse IgG conjugated to Alkaline Phosphatase (DAKO, 1:1000) was added and incubated 1 hour at RT on agitation. The plates were washed followed by addition of substrate (4-Nitrophenyl phosphatise disodium salt hexahydrate, SIGMA, 1 mg/ml), 100 µl/well. The plates were thereafter incubated at RT on agitation and absorbance at 405 nm measured consecutively for 30 min. Absorbance at 0 min was taken as background signal.

Results & Conclusions

Results are shown in FIG. 1

The exemplary antibodies, CAN03 and CAN04, were found to possess the highest binding signal for human IL1RAP.

B. Binding of Exemplary Antibodies to IL1RAP-Expressing Cells (i) Flow Cytometry Study-Anti-IL1RAP Antibodies of Murine Origin Materials & Methods Chronic myeloid leukaemia (CML) cell line KU812 cells were stained with antibodies raised against IL1RAP or a relevant isotype control. For detection, a secondary anti-mIg-APC was used.

The two exemplary antibodies (CAN03 and CAN04) was tested along with six comparator anti-IL1RAP antibodies (CAN01, CAN02, CAN05, CAN07, CAN08 and CAN09). An isotype negative control antibody was also included.

Results & Conclusions

Figure 2:
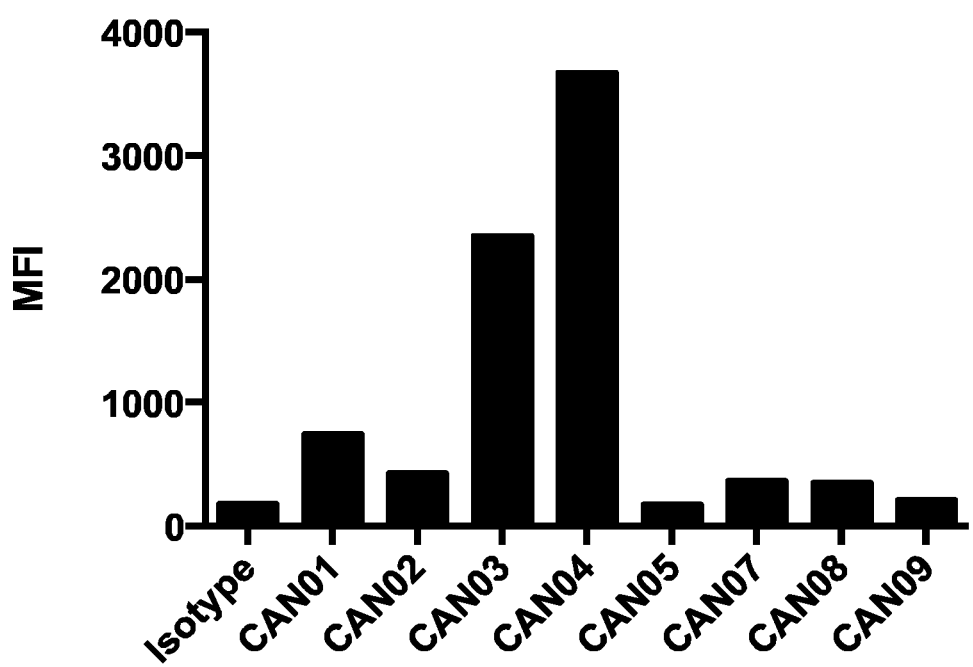
FIG. 2. Binding of exemplary antibodies to human IL1RAP-expressing KU812 CML cells. The graph shows the mean fluorescence intensity (MFI) value as measured by flow cytometry of KU812 cells stained with IL1RAP-targeting monoclonal antibodies at a concentration of 0.1 µg/mL. The exemplary antibodies of the invention, CAN03 and CAN04, has the highest MFI of the compared antibodies.

Staining of IL1RAP-expressing KU812 leukaemia cells reveals a higher mean fluorescence intensity (MFI) for CAN03 and CAN04 compared to the isotype control and other comparator antibodies targeting IL1RAP (FIG. 2).

C. Epitope/Domain Mapping of Exemplary Anti-IL1RAP Antibodies

Materials & Methods

In order to understand where the different antibody clones bind on IL1RAP, a structural analysis of the protein was performed revealing that the extracellular part of the receptor could be divided into three distinct domains hereafter referred to as domains 1, 2 and 3 (D1, D2, D3) (see Wang et al., 2010, *Nature Immunology*, 11:905-912, the disclosures of which are incorporated herein by reference). In order to determine the domain-binding pattern for the different antibody clones, a series of receptor constructs were generated and binding to these tested in an ELISA assay.

An indirect ELISA assay was performed. All samples were analysed in duplicate. Nunc-MaxiSorp 96 Micro Well™ Plates were coated with 100 ng of Rec hIL1RAP Domain123 (aa21-367) (positive control), Rec hIL1RAP Domain12 (aa21-234), Domain1 (aa21-134) or Rec hIL1RAP Domain3 (aa235-367) (100 µl/well) diluted in 0.01M PBS, pH 7.4, and incubated overnight at 4° C. Plates were washed with ELISA washing buffer (0.01M PBS, 0.05% Tween 20, pH 7.4) followed by a blocking step using 150 µl/well of ELISA blocking solution (PBS, 0.5% BSA, 0.05% Tween 20, pH 7.4). After 1 h incubation at room temperature (RT) on agitation the plates were washed again using ELISA washing buffer. CAN01, CAN03, CAN04, CAN05, CAN07, CAN08 and KMT-1 (positive control) were diluted in three-fold serial dilution (ranging from 1000 ng/ml to 0.5 ng/ml) in ELISA blocking solution and then transferred to the ELISA plate, 100 µl/well. Plates were incubated at RT for 1 h on agitation and then washed with ELISA washing solution. 100 µl/well of rabbit anti-mouse IgG conjugated to Alkaline Phosphatase (DAKO, 1:1000) was added and incubated 1 hour at RT on agitation. The plates were washed followed by addition of substrate (4-Nitrophenyl phosphatise disodium salt hexahydrate, SIGMA, 1 mg/ml), 100 µl/well. The plates were thereafter incubated at RT on agitation and absorbance at 405 nm measured consecutively for 30 min. Absorbance at 0 min was taken as background signal.

The exemplary antibodies of the compositions of the invention (CAN03 and CAN04) were tested along with eight comparator anti-IL1RAP monoclonal antibodies (CAN01, CAN02, CAN05, CAN07, CAN08, CAN10, and CAN11, together with a polyclonal anti-IL1RAP antibody (KMT-1) as a positive control.

Results & Conclusions

The majority of anti-IL1RAP antibodies tested for target validation bind to domain 3 (D3) while the exemplary CAN04 antibody of the invention is distinct in that it binds to domain 2 (D2). Hence, the exemplary antibodies (CAN03 and CAN04) bind to different domains (D3 and D2 respectively) of IL1RAP. The entire domain mapping data can be found summarized in the Table 4 below.

TABLE 4

Epitope mapping of exemplary anti-IL1RAP antibody clones.

| Clone | Domain123 (aa21-367) | Domain12 (aa21-234) | Domain1 (aa21-134) | Domain3 (aa235-367) | Suggested epitope |
|---|---|---|---|---|---|
| CAN03 | + | | | + | D3 |
| CAN05 | + | + | + | | D1 |
| CAN07 | + | | | + | D3 |
| CAN08 | + | | | + | D3 |
| CAN04 | + | + | | | D2 |
| CAN01 | + | | | + | D3 |
| CAN02 | + | | | | nd* |
| KMT-1 | + | + | + | + | polyclonal | nd* = not determined as epitope mapping data could not clearly identify specific domain for these constructs, which may be attributed to binding to a structural epitope containing sequence elements from more than one domain, e.g. D2-D3 junction.

D. Specificity/Cross-Reactivity of Exemplary Anti-IL1RAP Antibodies

Materials & Methods

An important feature of good lead candidate antibodies is that they cross-react with equal or near-equal potency to the homologous protein in a relevant toxicology species. According to the general regulatory guidelines, binding to one rodent and one non-rodent would be the preferred scenario, but for antibodies this is rarely the case, and instead many labs struggle to identify any relevant toxicology species except for primates.

For the present study, cross reactivity to non-human primates like *Macaca mulatta* (rhesus) or *Macaca fascicularis* (cynomolgus) was expected since the IL1RAP protein in these species share 99% homology to the human IL1RAP protein.

A number of potential lead antibodies were selected and tested for binding to recombinant *M. fascicularis* IL1RAP (aa21-367) in an ELISA assay.

The exemplary antibodies (CAN03 and CAN04) were tested along with seven comparator anti-IL1RAP monoclonal antibodies (CAN01, CAN02, CAN07, CAN08, CAN09, Mab676 from R&D, and a polyclonal anti-IL1RAP antibody (KMT-1).

Results & Conclusions

Surprisingly, several of the comparator anti-IL1RAP antibodies tested were found not to cross-react with cynomolgus IL1RAP, amongst them the commercial reference antibody mAb676 from R&D, Table 5. CAN03 and CAN04 do however both react with the cynomolgus protein.

TABLE 5

Binding to cynomolgus IL1RAP.

| Clone | Binding to rec. M. fascicularis IL1RAP ($OD_{405}$) |
| --- | --- |
| CAN01 | 0.324 |
| CAN02 | 0.014 |
| CAN09 | 0.022 |
| CAN03 | 0.870 |
| CAN04 | 0.416 |
| CAN07 | 0.111 |
| CAN08 | 0.375 |
| mAb676 (R&D) | 0.037 |
| KMT-1 | 0.481 |

Values in bold denotes clones identified to cross-react with IL1RAP from M. fascicularis.

E. Inhibition of IL-1β, IL-33, IL-36α Signalling by Exemplary Anti-IL1RAP Antibodies
(i) Effect of Different Antibodies and Antibody Combinations on IL-1 and IL-33 Signalling in the HEK-Blue IL-33/IL-1β Cell Line Materials & Methods As IL1RAP is a functional part of both the IL-1 and the IL-33 receptor complexes, antibodies binding to IL1RAP may also inhibit IL-1 and IL-33 signalling.

In order to test for the capability of potential lead candidate antibodies to block IL-1 and IL-33 signalling, an IL-1 and IL-33 dependent reporter gene assay was set up. HEK-Blue IL-33/IL-1β cells (InvivoGen) respond to IL-1 or IL-33 signalling by the release of alkaline phosphatase that can be quantified by a colorimetric assay. To test the inhibitory capacity of the lead candidates HEK-Blue cells were plated at 50 000 cells/well and incubated with the test antibodies 45 minutes prior to stimulation with IL-1β or IL-33 in a final concentration in assay of 0.3 ng/ml for each ligand. Final assay concentrations of antibodies were 200 nM-0.01 nM. In the control wells, the antibodies were replaced by PBS. The cells were incubated at 37° C. o/n before measuring the amount of alkaline phosphatase released.

The exemplary antibodies of the invention (CAN03 and CAN04) were tested alone and in 1:1 combination for inhibition of IL-1β and IL-33 signalling.

Results & Conclusions

Figure 3A:
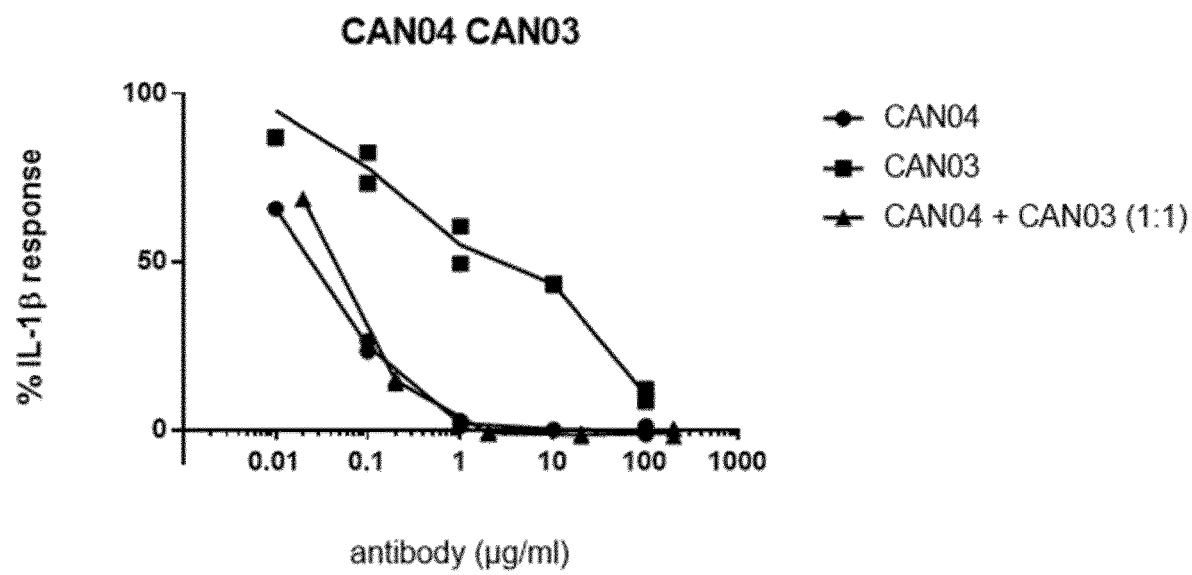
FIG. 3. Ability of the exemplary antibodies CAN03 and CAN04 and their combination to block IL-1β or IL-33 signalling in a IL-1/IL-33-responsive HEK reporter system. (A) Both CAN03 and CAN04 blocks IL-1β signalling completely although CAN04 has superior potency. The combination of CAN03 and CAN04 (1:1) has the same efficacy and potency as CAN04 on its own. (B) CAN03 and CAN04 inhibits IL-33 signalling with 70% (CAN03) or 50% (CAN04) efficacy. The combination of CAN03 and CAN04 (1:1) shows a synergistic increase in both potency and efficacy compared to the antibodies alone.

As depicted in FIG. 3A, the exemplary antibody CAN04 induced a pronounced inhibition of IL-1β signalling. Exemplary antibody CAN03 also inhibited signalling but with less potency than CAN04. When CAN04 and CAN03 were combined, an inhibition similar to that of CAN04 alone was detected.

Figure 3B:
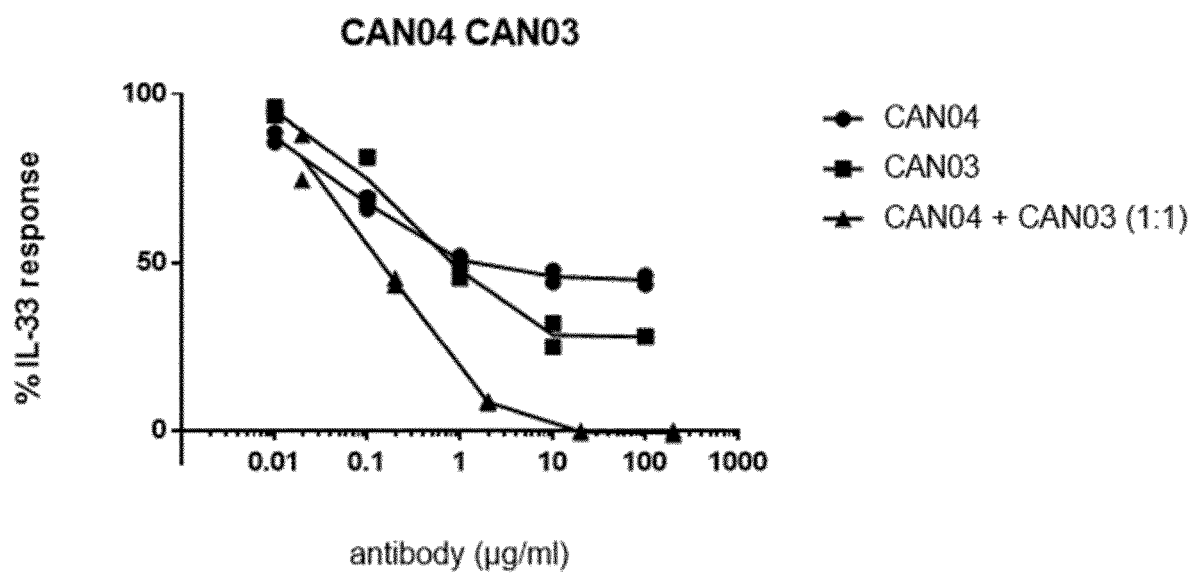

In contrast to the inhibition of IL-1β signalling, CAN03 and CAN04 when administered alone did not completely inhibit IL-33 signalling. Both antibodies blocked signalling with comparable potency but could inhibit only ~70% (CAN03) or ~50% (CAN04) of the signal (FIG. 3B). Surprisingly however, the combination of CAN03 and CAN04 (1:1) inhibited the signal to 100% and was more potent compared to each antibody alone. Thus, two antibodies binding different domains of IL1RAP (CAN03 to D3, CAN04 to D2) act synergistically to inhibit IL1RAP signalling.

(ii) Effect of Different Antibodies and Antibody Combinations on IL-36 Signalling in a IL-1Rrp2-Transfected HEK-Blue IL-33/IL-1β Cell Line Materials & Methods As IL1RAP also is a functional part of both the IL-36 receptor complex, antibodies binding to IL1RAP may also inhibit IL-36 signalling.

The HEK-Blue IL-33/IL-1β system (InvivoGen) does not respond to IL-36 since it lacks the IL-36 receptor (IL1Rrp2). In order to test for the capability of potential lead candidate antibodies to block IL-36 signalling, the HEK-Blue IL-33/IL-1β system was modified by transfection with IL1Rrp2 (the IL36-receptor) which allowed IL-36-induced reporter gene expression. HEK-Blue cells were transiently transfected with an IL1Rrp2-expressing vector using Lipofectamine LTX (ThermoFisher), cultured for 24 h, plated at 50 000 cells/well and incubated with the test antibodies 45 minutes prior to stimulation with IL-36α at different concentrations. Assay concentrations of antibodies were 0.1, 1 and 10 μg/ml. In the control wells, the antibodies were replaced by PBS. The cells were incubated at 37° C. o/n before measuring the amount of alkaline phosphatase released.

The exemplary antibodies (CAN03 and CAN04) were tested alone and in 1:1 combination for inhibition of signalling.

Results & Conclusions

Figure 4A:
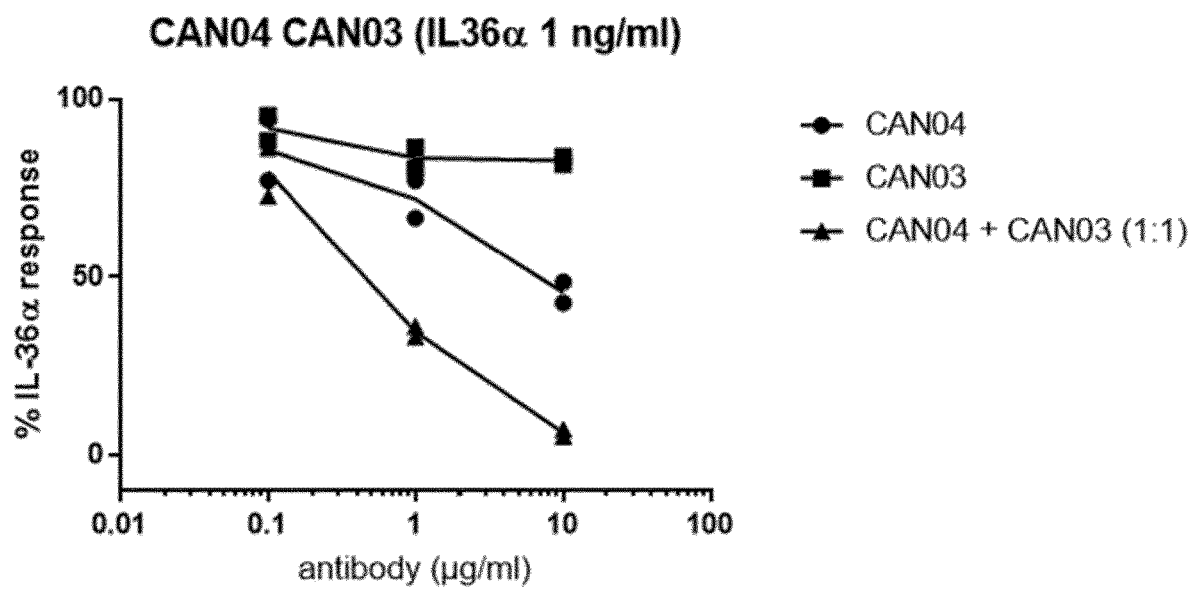
FIG. 4. Ability of the exemplary antibodies CAN03 and CAN04 and their combination to block IL-36α signalling in a IL-36-responsive modified HEK reporter system. CAN04 at the maximum tested concentration blocks IL-36α signalling to 45% of the signal at 1 ng/ml IL-36α (A) and to 75% at 10 ng/ml (B), CAN03 has very little effect at both concentrations of IL-36α. The combination of CAN03 and CAN04 (1:1) however shows a synergistic increase in both potency and efficacy compared to the antibodies alone.
Figure 4B:
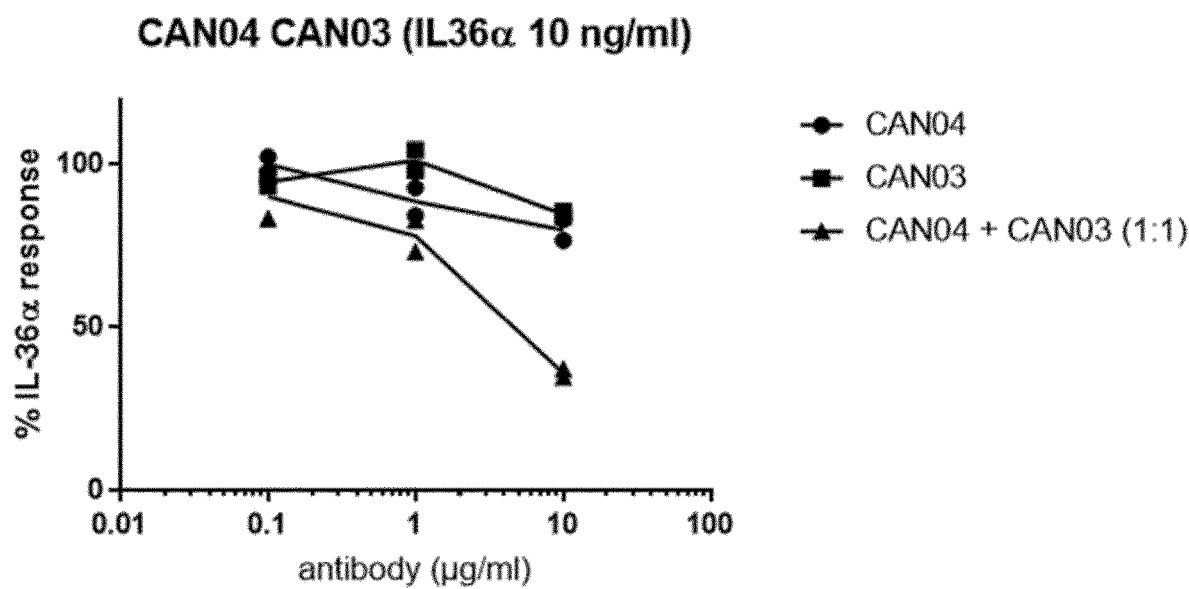

As depicted in FIGS. 4A and 4B, the exemplary antibody CAN04 on its own induced a moderate inhibition of IL-36α signalling at 1 ng/ml IL-36α and very little inhibition at 10 ng/ml IL-36α. The exemplary antibody CAN03 on its own did not inhibit signalling at those concentrations of IL-36α. However, the combination of CAN03 and CAN04 (1:1) was more potent compared to each antibody alone and resulted in a synergistic inhibition of the IL-36α signal. Thus, also for IL-36 signalling, two antibodies binding different domains of IL1RAP act synergistically to inhibit IL1RAP signalling.

(iii) Effect in Cell Lines

Materials & Methods

In order to test the ability to inhibit IL1RAP-dependent signalling in a cancer cell model, an IL-1 dependent cellular assay was set up. The IL1RAP-expressing breast cancer cell line Hs578T responds to IL-1β stimulation with IL-6 production and was used to test the inhibitory effect of the exemplary antibodies and an isotype control. Cells were plated at 20 000 cells/well in 12-well plates and incubated with 0.1 ng/ml IL1B for 24 hours. IL-6 in the supernatant was measured by ELISA. Cells were incubated with or without the indicated antibodies and stimulated with IL-1B. The final assay concentration of antibodies was 10 μg/ml (10

μg/ml of each antibody when tested alone, 5 μg/ml of each when tested in 1:1 combination).

Results & Conclusions

Figure 5:
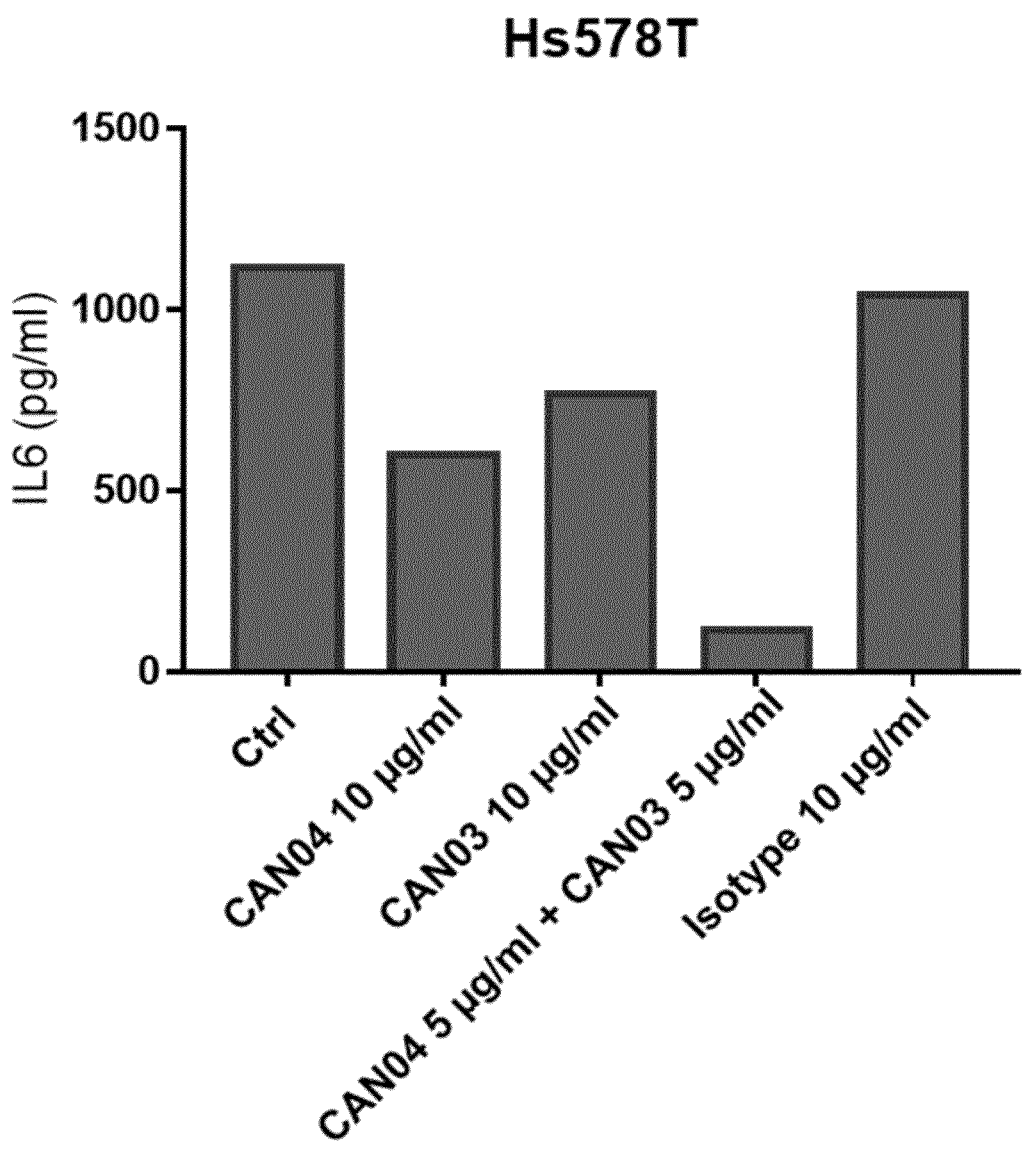
FIG. 5. Ability of the exemplary antibodies CAN03 and CAN04 and their combination to block IL-1β induced IL-6 production in the Hs578T (HTB-126) breast cancer cell line. Cells were stimulated with IL1B in the presence or absence of the indicated antibodies. CAN03 and CAN04 at 10 µg/ml inhibits IL-6 production to 70% (CAN03) or 50% (CAN04) of the control while the combination of CAN03 and CAN04 (at 5+5 µg/ml) shows a synergistic increase in inhibition to 10% of control.

As depicted in FIG. 5, stimulation with IL-1β in the presence of CAN04 or CAN03 at 10 μg/ml led to a 50% (CAN04) or 30% (CAN03) inhibition of IL-6 production after 24 h, while the isotype control antibody did not have any effect. As in the HEK-Blue IL-33/IL-1β system in example D, the combination of CAN04 and CAN03 (5 μg/ml CAN04+5 μg/ml CAN03) led to a synergistic increase in effect and 90% of the signal could be inhibited. Thus, CAN03 and CAN04 act synergistically when combined to reduce a natural response to IL-1β stimulation in a breast cancer cell line.

F. Screening of Antibodies to Domain 1, 2 and 3 of IL1RAP (i) Screening for Binding to IL1RAP Antibodies generated towards IL1RAP are screened as in Example A (ii) above for binding to IL1RAP and subsequently as in Example B (i) for binding to cells expressing high levels of cell surface IL1RAP (such as KU812 CML cells or SK-MEL-5 melanoma cells).

(ii) Analysis of Binding to Different Domains

Antibodies that react with IL1RAP are tested for interaction with D1, D2 and D3 as described as in Example C.

(iii) Analysis of Competitive Binding by ELISA

To verify binding to similar regions of IL1RAP as CAN03 (D3) or CAN04 (D4), competitive ELISAs may be performed as described below.

Protocol

All samples are analysed in duplicate.
Coat a Nunc-MaxiSorp 96 Micro Well™ Plate with 100 μl/well of recombinant hIL1RAP 21-367 (1 ug/ml) diluted in 0.01M PBS, pH 7.4.
Incubate the plate overnight at 4° C.
Wash the plate with ELISA washing buffer
(0.01M PBS, 0.05% Tween 20, pH 7.4).
Add 150 μl/well of ELISA blocking solution
(PBS, 0.5% BSA, 0.05% Tween 20, pH 7.4).
Incubate the plate for 1 h at room temperature (RT) under agitation.
Wash the plate with ELISA washing buffer.
Add samples of test items (e.g. mAb 1, mAb 2) to wells (100 μl/well, 10 μg/ml)
Incubate the plate for 1 h at RT.
Wash the plate with ELISA washing solution.
Add a solution of reference antibodies CAN03 or CAN04 (100 μl/well, 1 μg/ml) to all wells.
Incubate the plate for 1 h at RT.
Wash the plate with ELISA washing buffer.
Add 100 μl/well of a suitable secondary antibody conjugated to Alkaline rabbit anti-mouse IgG conjugated to Alkaline Phosphatse (If the test items are human antibodies, a suitable secondary antibody would be Goat Anti-Mouse IgG (Fc specific)—Alkaline Phosphatase antibody, SIGMA, A1418)
Incubate the plate for 1 h at RT under agitation.
Wash the plate with washing buffer.
Add 100 μl of pNPP substrate per well.
(4-Nitrophenyl phosphatise disodium salt hexahydrate, SIGMA, 1 mg/ml).
Incubate the plate at RT under agitation and measure absorbance at 405 nm consecutively for 30 min. Absorbance at 0 min should be taken as background signal.

G. Affinity Maturation of Antibodies

Antibodies generated towards IL1RAP and selected for binding to IL1RAP and D2 or D3 respectively may be "affinity-matured" for increased affinity.

Affinity-matured antibodies are produced by procedures known in the art. Many of these methods are based on the general strategy of generating panels or libraries of variant proteins by mutagenesis followed by selection and/or screening for improved affinity. Mutagenesis is often performed at the DNA level, for example by error prone PCR (Thie, Voedisch et al. 2009, Methods Mol Biol 525:309-322), by gene shuffling (Kolkman and Stemmer 2001, Nat Biotechnol. May; 19 (5):423-8), by use of mutagenic chemicals or irradiation, by use of 'mutator' strains with error prone replication machinery (Greener 1996, In Vitro Mutagenesis Protocols. Humana press, NJ) or by somatic hypermutation approaches that harness natural affinity maturation machinery (Peled, Kuang et al. 2008, Annu Rev Immunol. 26:481-511). Mutagenesis can also be performed at the RNA level, for example by use of Q13 replicase (Kopsidas, Roberts et al. 2006, Immunol Lett. 2006 Nov. 15; 107 (2):163-8). Random mutagenesis of HVR and/or framework residues is described by: Barbas et al., Proc. Nat. Acad. Sci. USA 91:3809-13 (1994); Schier et al. Gene 169:147-55 (1995); Yelton et al. J. Immunol. 1 55:1 994-2004 (1995); Jackson et al., J. Immunol. 154 (7):331 0-19 (1995); and Hawkins et al. J. Mol. Biol. 226:889-96 (1992); Johnson & Hawkins, Affinity Maturation of Antibodies Using Phage Display, Oxford University Press 1996.

Library-based methods allowing screening for improved variant proteins can be based on various display technologies such as phage, yeast, ribosome, bacterial or mammalian cells, and are well known in the art (Benhar 2007, Expert Opin Biol Ther. May; 7 (5): 763-79). Affinity maturation can be achieved by more directed/predictive methods for example by site-directed mutagenesis or gene synthesis guided by findings from 3D protein modeling (see for example Queen, Schneider et al. 1989, PNAS, 86 (24): 10029-33 or U.S. Pat. No. 6,180,370 or U.S. Pat. No. 5,225,539). Marks et al. Bio/Technology 10:779-83 (1992) describes affinity maturation by $V_H$ and $V_L$ domain shuffling.

H. Production of Bi-Epitopic Antibodies for Binding to Different Domains of IL1RAP.

Materials & Methods

The bispecific antibody 2C9x3F8 has been produced by controlled Fab-arm exchange (cFAE), described by Labrijn et al (Proc Natl Acad Sci USA. 2013-3-26; 110 (13): 5145-5150). The process involves the expression of two separate parental antibodies, each containing a single point mutation, F405L and K409R in the respective CH3 domains (EU-numbering convention as described in Kabat et al., Sequences of Proteins of Immunological Interest, 5th Ed. Public Health Service, National Institutes of Health, Bethesda, MD. (1991)). The parental antibodies were mixed and subjected to controlled reducing conditions in vitro that separated the antibodies into Heavy chain/Light chain half-molecules (Fab-arms). After re-oxidation, the Fab-arms will reassembly. AS explained above, the point mutations in the antibodies CH3 domains will affect the reassembly process in a way that highly pure bsAbs will be formed.

For bsab2C9x3F8, the parental antibodies were ch2C9 (representing CAN03) and hu3F8 (representing CAN04). The ch2C9 is a chimeric monoclonal antibody with mouse VL and VH and human constant parts (IgG1/kappa). hu3F8 is a humanized IgG1/kappa monoclonal antibody. p2C9H4hG1 is an expression vector containing all the genetic elements required to express ch2C9 heavy chain in mammalian cells. The point mutation F405L was introduced to p2C9H4hG1 and the new expression vector was named p2C9-HC-hIgG1-F405L. p3F8-VH-v2 is an expression vector containing all the genetic elements required to express hu3F8 heavy chain in mammalian cells. The point mutation K409R was introduced to p3F8-VH-v2 and the new expression vector was named p3F8-HC-hIgG1-K409R. p2C9K9hK is an expression vector containing all the genetic elements required to express ch2C9 light chain in mammalian cells and p3F8-VL-v2 is an expression vector containing all the genetic elements required to express hu3F8 light chain in mammalian cells Mutagenesis: To introduce the F405L or K409R mutations, p2C9H4hG1 and p3F8-VH-v2 were double digested with Bst EII and Nsi I and synthetic gene strings (Geneart) containing the point mutations were cloned to the linearized vectors by In-Fusion cloning methodology (Clontech).

Antibody production: ch2C9-F405L and hu3F8-K409R monoclonal antibodies were produced by co-transfecting relevant heavy and light chain expression vectors in Freestyle 293F cells (Life Techologies), according to the manufacturer's instructions. The following vectors were used: ch2C9-F405L; HC vector p2C9-HC-hIgG1-F405L and LC vector p2C9K9hK; hu3F8-K409R; HC vector p3F8-HC-hIgG1-K409R and LC vector p3F8-VL-v2.

Purification: Antibodies were purified by protein A affinity chromatography. Cell culture supernatants were applied to MabSelect SuRe columns (GE Healthcare), washed with PBS and eluted with 0.1 M Glycine, pH 3.0. The eluate was neutralized directly during fraction collection by 1.0 M Tris-HCl, pH 9.0. Immediately after purification, the buffer was exchanged to PBS, pH 7.4, by gel filtration with PD-10 columns (GE Healthcare). Purity was determined by SDS-PAGE and concentration was measured by absorbance at 280 nm. Purified antibodies were stored at 4° C.

Controlled Fab-arm exchange: The bispecific antibodies were generated by a chemical reaction where equimolar amounts of ch2C9-F405L and hu3F8-K409R were mixed to a final concentration of 0.5 mg/mL each, in presence of 75 mM 2-mercaptoethylamin-HCL (2-MAE, Sigma) and incubated at 31° C. for 5 hours. After removal of 2-MAE by ultrafiltration (Viva-spin 6.10 kDa, Satorius) the samples were stored over night at 4° C. to allow reoxidation of the disulfide bonds.

Results & Conclusions

The present example demonstrates that pure antibodies directed to two different domains of IL1RAP can be produced.

I. Humanization of Monospecific and Bi-Epitopic Antibodies

It is not always desirable to use non-human antibodies for human therapy, thus the antibody according to the invention may be a human antibody or a humanized antibody.

Humanization is performed, e.g., by following the method of Winter and co-workers (Jones et al., Nature, 321:522-525 (1986); Riechmann et al., Nature, 332:323-327 (1988); Verhoeyen et al., Science, 239:1534-1536 (1988)), by substituting rodent CDRs or CDR sequences for the corresponding sequences of a human antibody. (See also U.S. Pat. No. 5,225,539). In some instances, Fv framework residues of the human immunoglobulin are replaced by corresponding non-human residues. Humanized antibodies also comprise, e.g., residues which are found neither in the recipient antibody nor in the imported CDR or framework sequences. In general, the humanized antibody includes substantially all of at least one, and typically two, variable domains, in which all or substantially all of the CDR regions correspond to those of a non-human immunoglobulin and all or substantially all of the framework regions are those of a human immunoglobulin consensus sequence. The humanized antibody optimally also includes at least a portion of an immunoglobulin constant region (Fc), typically that of a human immunoglobulin (Jones et al., 1986; Riechmann et al., 1988; and Presta, Curr. Op. Struct. Biol., 2:593-596 (1992)).

J. In Vitro and In Vivo Activity of Bispecific or Combinations of Monospecific Antibodies Monospecific antibodies, combinations of monospecific antibodies or bispecific antibodies may be tested in the HEK-system described in Example E for inhibition of IL-1, IL-33 or IL-36 signalling. The monospecific antibodies, combinations of monospecific antibodies or bispecific antibodies can also be tested for inhibition of IL-1, IL-33 or IL-36 signalling in cell lines (as for example in Example E) or primary cells that have the appropriate receptors. Readout in the latter systems can be activation of intracellular signalling pathways (including NFκB) or downstream cytokines or other induced proteins.

The monospecific antibodies, combinations of monospecific antibodies or bispecific antibodies can also be tested for inhibition of LPS-induced inflammation of human cells ex vivo. LPS is administered to $2 \times 10^5$ human PBMCs in the absence or presence of the monospecific antibodies, combinations of monospecific antibodies or bispecific antibodies and the supernatant is analysed for IL-6 and other cytokines (such as IL-1β, TNFα and IL-8) after incubation at 37° C. for 6, 24 and 48 hours. Blocking of IL-1 signalling in this system reduces inflammatory signalling and secretion of cytokines such as IL-6.

The monospecific antibodies, combinations of monospecific antibodies or bispecific antibodies can also be tested in IL-1, IL-33 and/or IL-36-dependent disease models in vivo. One such example is Xenotransplant models of Psoriasis, conducted e.g. as described in WO 2013/074569; where human skin biopsies from psoriasis patients are transplanted onto immunodeficient mice (e.g. SCID mice) and allowed to engraft for at least four weeks. The transplanted grafts show histological features that are similar to psoriasis, including features such as epidermal thickening that can be used as a measure for treatment effects. In order to increase inflammation and the pathological features of psoriasis, autologous T cells derived from the donor's psoriatic plaques can be administered intra-dermally or intravenously into the grafted mice. An alternative to injection of T cells is intradermal injection of autologous PBMCs that are stimulated with *Staphylococcus* enterotoxins (SEB and/or SEC) and IL-2. A few weeks after injection of cells, the grafts are analysed by histology, the epidermal thickness is measured and treatment effects are calculated. Other psoriasis models applicable to the present invention are described in Gudjonsson et al (2007) J Invest Der, 127:1292-1308 and Kundu-Raychaudhuri et al (2014) Indian J Dermatology, Venereology, and Leprology 80 (3): 204-213.

Materials

The following study was conducted to determine whether the monoepitopic antibody CAN04 and the bi-epitopic antibody bsACAN03xCAN04 were able to inhibit IL-1β and IL-33 signalling.

Preparation of Antibodies

All antibodies were diluted in PBS for testing. Working solutions for reporter gene assay, HEK-Blue IL-33/IL-1β were made in PBS at 20 times at the final assay concentration. The final assay volume was 200 µl (containing 10 µl antibody or diluent (PBS)+180 µl cells+10 µl ligand). Final assay concentrations of antibodies were as follows; 10 to 0.0001 nM (by serial dilutions in 3-fold dilutions steps).

Preparation of Human Ligands (IL-1β and IL-33)

IL-13 and IL-33 were diluted in PBS to a stock concentration of 10 µg/mL. Stock concentrations of 10 µg/mL of the ligands were stored in aliquots at −80° C. until use. For the reporter gene assay, the ligands were used at a final concentration of 100 ng/ml for hIL-1β and 2 ng/ml for hIL-33; these concentrations gave 70-80% of the maximal effect in the assay as determined in a pre-test experiment.
Dilution of Ligands to Final Assay Concentration
  (a) hIL-1β, 100 ng/ml
    Stock of ligands 10 µg/mL was diluted 1:5 (200 µl+800 µl Selective medium, see below)=2000 ng/ml
    2000 ng/ml was diluted 1:20 in the assay; 10 µl of LPS 2000 ng/ml+190 µl cells and compound/well to yield a final concentration of 100 ng/ml
  (b) hIL-33, 2 ng/ml
    Stock of ligands 10 µg/mL was diluted 1:250 (10 µl+2490 µl Selective medium, see below)=40 ng/ml
    40 ng/ml was diluted 1:20 in the assay; 10 µl of LPS 200 ng/ml+190 µl cells and compound/well to yield a final concentration of 2 ng/ml
Cell Line
HEK-Blue IL-33/IL-1β cells, generated by stable transfection of HEK-Blue™ IL-1β cells with the IL1RL1, were used as IL-33/IL-1β sensor cells (Cat no. hkb-IL-33, InvivoGen, San Diego, US).

Methods

Study Design

Stock solutions of the antibodies were prepared in PBS. Working solutions for reporter gene assay, HEK-Blue IL-33/IL-1 β were made in PBS at 20 times at the final assay concentration. The final assay volume was 200 µl (containing 10 µl antibody or diluent (PBS)+180 µl cells+10 µl ligand). Final assay concentrations of antibodies were as follows; 10 to 0.0001 nM (by serial dilutions in 3-fold dilutions steps. In control wells (stimulated/unstimulated cells) antibodies were replaced by 10 µl PBS.
Culturing and Stimulation of HEK-Blue IL-33/IL-1β Cells
As IL1RAP is a functional part of the IL-1 receptor complex, antibodies binding to IL1RAP have the potential to inhibit IL-1 signalling. Since tumour cells have been reported to use IL1RAP dependent ligands such as IL-13 and IL-33 as a growth factor, blocking this signal may provide an important mechanism for mediating anti-tumour effects (either separately or combined with an ADCC effect). In order to test for the capability of antibodies to block IL-1 signalling, an IL-1 dependent reporter gene assay was set up. HEK-Blue IL-33/IL-13 cells (InvivoGen) respond to IL-1 signalling by the release of alkaline phosphatase that can be quantified by a colorimetric assay. To test the inhibitory capacity of the lead candidates HEK-Blue cells were plated at 50 000 cells/well and incubated with the test antibodies 45 minutes prior to stimulation with human IL-1α, IL-1β, and IL-33 in a final concentration to give optimal stimulation. Final assay concentrations of antibodies were 10 nM-0.0001 nM. In control wells, antibodies were replaced by PBS. The cells were incubated at 37° C. o/n before measuring the amount of alkaline phosphatase released by QUANTI-Blue-Medium for detection and quantification of alkaline phosphatase.

The HEK-Blue IL-33/IL-1β cells were thawed and cultured in DMEM, 10% FCS (HI) and PEST and Normocin for two passages. After two passages the cells were cultured with selection antibiotics (Zeocin, HygroGold and Blasticidin) added to the medium above for at least one passage before the experiments, as well as during the experiments. HygroGold is required to maintain the IL-1β specificity to the cell line and Blasticidin and Zeocin are required to maintain the plasmids encoding IL1RL1 and SEAP respectively. The experiments were run on cells of 70% confluency. The cells were split 2-3 times/week, or when they had reached 80-90% confluence.

The ligands were titrated in a dose range from 300 ng/ml to 0.01 ng/ml. To generate a good assay for testing the antibodies ability to affect the IL-1 signalling (stimulate or inhibit the amount of alkaline phosphatase release) a concentration that resulted in a robust signal on the linear slope of the dose-response curve is preferred. For this system a concentration of 100 ng/ml for hIL-1β and 2 ng/ml for hIL-33 were selected.

Evaluation of Results

Raw data was converted to % inhibition using equation 1:

% inhibition=(1−(A−B)/(C−B))×100 wherein:
A=Ligand activity with compound dissolved in PBS added
B=Negative control, No Ligand, only PBS (vehicle)
C=Positive control, Ligand with PBS (vehicle),
IC50 Represents the Concentration Yielding 50% Inhibition of the Maximal Response.
EC50 represents the concentration yielding an inhibition representing 50% inhibition with respect to calculated values for the top and bottom of the curve.

CONCLUSIONS & RESULTS

Figure 6:
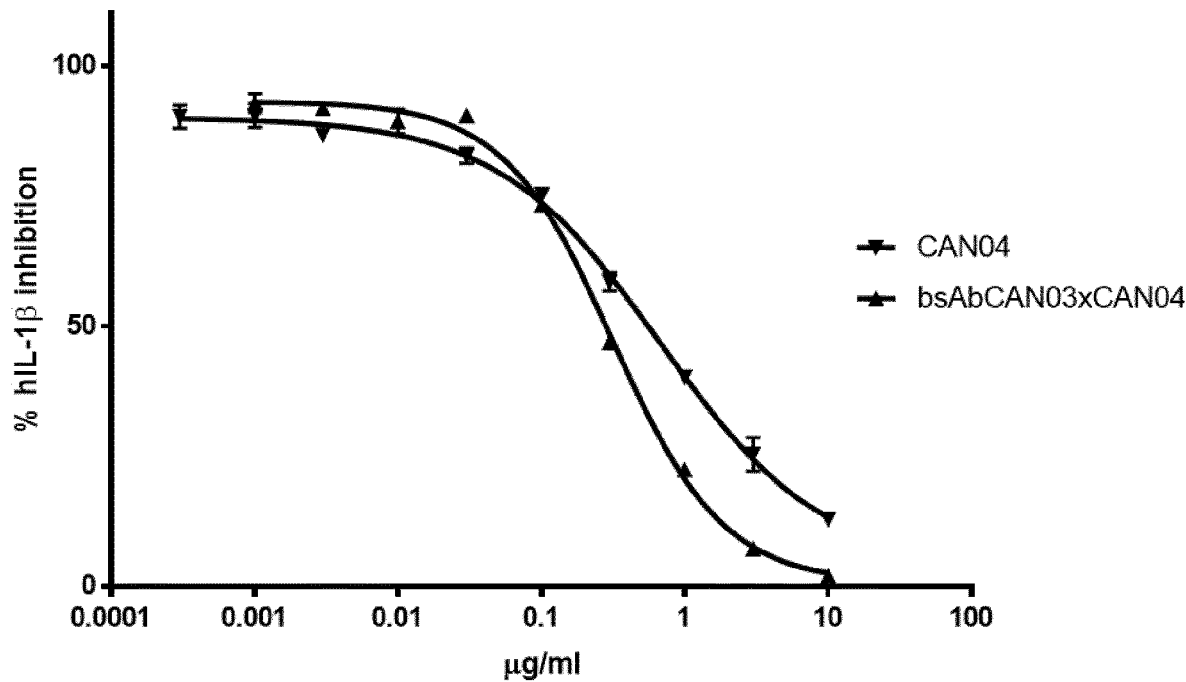
FIG. 6. Ability of the exemplary bi-epitopic antibody bsACAN03xCAN04 (containing one CAN04 VH/VL domain and one CAN03 VH/VL domain) and CAN04 to block IL-1β or IL-33 signalling in a IL-1/IL-33-responsive HEK reporter system. (A) CAN04 as well bsACAN03xCAN04 blocks IL-1β signalling completely. (B) CAN04 inhibits IL-33 signalling although with partial efficacy. Inclusion of the CAN03 domain in the bi-epitopic bsACAN03xCAN04 antibody however allows for complete inhibition of IL-33 signalling.
Figure 6:
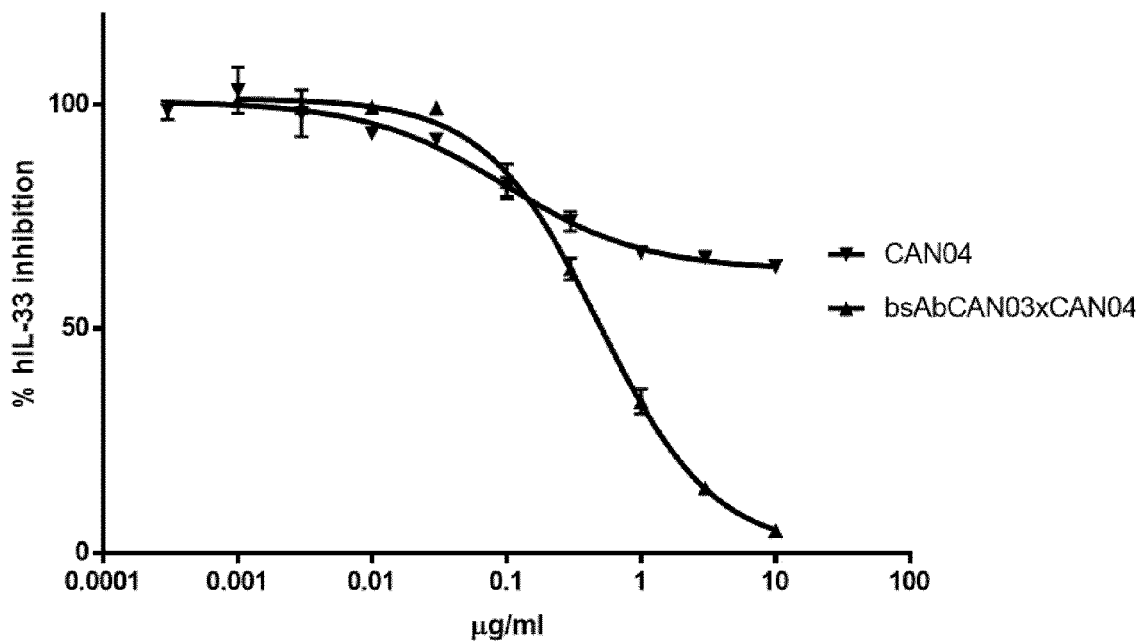

The present example demonstrates that the monoepitopic antibody CAN04, as well the biepitopic bsACAN03xCAN04 block IL-1β signalling completely. CAN04 also inhibits IL-33 signalling but with partial efficacy. The bi-epitopic bsACAN03xCAN04 antibody however allows for complete inhibition of IL-33 signalling as illustrated in FIG. 6.

Overview of sequences

SEQ ID NO: 1: CAN04 variant 6 variable light chain (VL)
DIQMTQSPSSLSASVGDRVTITCQASQGINNYLNWYQQKPGKAPKLLIHYTSGLHAGVP
SRFSGSGSGTDYTLTISSLEPEDVATYYCQQYSILPWTFGGGTKVEIKR

Overview of sequences

SEQ ID NO: 2: CAN04 variable light chain (VL) VL1
DIQMTQSPSSLSASVGDRVTITCSASQGINNYLNWYQQKPGKAPKLLIHYTSGLHAGVP
SRFSGSGSGTDYTLTISSLQPEDVATYYCQQYSILPWTFGGGTKVEIKR SEQ ID NO: 3: CAN04 variable light chain (VL) VL3
DIQMTQSPSSLSASVGDRVTITCQASQGINNYLNWYQQKPGKAPKLLIHYTSGLHAGVP
SRFSGSGSGTDFTLTISSLEPEDVATYYCQQYSILPWTFGGGTKVEIKR SEQ ID NO: 4: CAN04 variant 6 variable heavy chain (VH)
QVQLVQSGAEVKKPGSSVKVSCKASGYAFTSSWMNWVRQAPGQGLEWMGRIYPGD
GNTHYAQKFQGRVTLTADKSTSTAYMELSSLRSEDTAVYYCGEGYLDPMDYWGQGTL
VTVSS SEQ ID NO: 5: CAN04 variable heavy chain (VH) VH1
QVQLVQSGAEVKKPGSSVKVSCKASGYAFSSSWMNWVRQAPGQGLEWMGRIYPGD
GNTHYAQKFQGRVTLTADKSTSTAYMELSSLRSEDTAVYYCGEGYLDPMDYWGQGTL
VTVSS SEQ ID NO: 6: CAN04 variable heavy chain (VH) VH3
QVQLVQSGAEVKKPGSSVKVSCKASGYTFTSSWMNWVRQAPGKGLEWMGRIYPGDG
QTHYAQKFQGRVTLTADKSTSTAYMELSSLRSEDTAVYYCGEGYLDPMDYWGQGTLV
TVSS SEQ ID NO: 7: CAN04 variable heavy chain (VH) VH4
QVQLVQSGAEVKKPGSSVKVSCKASGYTFTSSWMNWVRQAPGKGLEWMGRIYPGDG
QTHYAQKFQGRVTITADKSTSTAYMELSSLRSEDTAVYYCGEGYLDPMDYWGQGTLVT
VSS SEQ ID NO: 8: CAN04 variant 6 Light chain CDR1 (according to Chotia)
SASQGINNYLN SEQ ID NO: 9: CAN04 variant 6 Light chain CDR2 (according to Chotia)
YTSGLHAGV SEQ ID NO: 10: CAN04 variant 6 Light chain CDR3 (according to Chotia)
QQYSILPWT SEQ ID NO: 11: CAN04 variant 6 Heavy chain CDR1 (according to Chotia)
GYAFTSSWMN SEQ ID NO: 12: CAN04 variant 6 Heavy chain CDR2 (according to Chotia)
RIYPGDGNTHYAQKFQG SEQ ID NO: 13: CAN04 variant 6 Heavy chain CDR3 (according to Chotia)
GYLDPMDY SEQ ID NO: 14: CAN03 variable light chain (VL)
DILLTQSPAILSVSPGERVSFSCRASQSIGTSIHWYQRRTNGSPRLLIKSASESISGIPSRF
SGSGSGTDFTLSINSVESEDIADYYCQQSNSWPTTFGAGTKLELKR SEQ ID NO: 15: CAN03 variable heavy chain (VH)
DVKLVESGGGLVKPGGSLKLSCAASGFTFSIYTMSWVRQTPEKRLEWVATISIGGSYIN
YPDSVKGRFTISRDNAKNTLYLQMSSLKSEDTAIYYCSREVDGSYAMDYWGQGTSVTV
SS SEQ ID NO: 16: CANO3 Light chain CDR1 (according to Chotia)
RASQSIGTSIH SEQ ID NO: 17: CANO3 Light chain CDR2 (according to Chotia)
SASESIS SEQ ID NO: 18: CANO3 Light chain CDR3 (according to Chotia)
QQSNSWPTT SEQ ID NO: 19: CAN03 Heavy chain CDR1 (according to Chotia)
GFTFSIYTMS SEQ ID NO: 20: CAN03 Heavy chain CDR2 (according to Chotia)
TISIGGSYINYPDSVKG SEQ ID NO: 21: CAN03 Heavy chain CDR3 (according to Chotia)
EVDGSYAMDY SEQ ID NO: 22: CAN04 variant 6 Variable light chain CDR2 (according to Kabat)
YTSGLHA -continued

| Overview of sequences |
|---|

SEQ ID NO: 23: CAN04 variant 6 Variable light chain CDR3 (according to Kabat)
QYSILPWT SEQ ID NO: 24: CAN04 variant 6 Variable heavy chain CDR1 (according to Kabat)
GYAFTSS SEQ ID NO: 25: CAN04 variant 6 Variable heavy chain CDR2 (according to Kabat)
YPGDGN SEQ ID NO: 26: CAN03 Variable light chain CDR3 (according to Kabat)
QSNSWPTT SEQ ID NO: 27: CAN03 Variable heavy chain CDR1 (according to Kabat)
GFTFSIY SEQ ID NO: 28: CAN03 Variable heavy chain CDR2 (according to Kabat)
SIGGSY SEQ ID NO: 29: CAN04 variant 6 Light chain CDR1 (according to Kabat)
ASQGINNYLN SEQ ID NO: 30: CAN03 Light chain CDR1 (according to Kabat)
ASQSIGTSIH SEQ ID NO: 31: CAN04 Heavy chain constant region
ASTKGPSVFPLAPSSKSTSGGTAALGCLVKDYFPEPVTVSWNSGALTSGVHTFPAVLQ
SSLYSLSSVVTVPSSSLGTQTYICNVNHKPSNTKVDKKVEPKSCDKTHTCPPCPAPELL
GCPSVFLFPPKPKDTLMISRTPEVTCVVVDVSHEDPEVKFNWYVDGVEVHNAKTKPRE
EQYNSTYRVVSVLTVLHQDWLNGKEYKCKVSNKALPAPIEKTISKAKGQPREPQVYTLP
PSREEMTKNQVSLTCLVKGFYPSDIAVEWESNGQPENNYKTTPPVLDSDGSFFLYSKL
TVDKSRWQQGNVFSCSVMHEALHNHYTQKSLSLSPGK SEQ ID NO: 32: CAN04 Light chain constant region
TVAAPSVFIFPPSDEQLKSGTASVVCLLNNFYPREAKVQWKVDNALQSGNSQESVTEQ
DSKDSTYSLSSTLTLSKADYEKHKVYACEVTHQGLSSPVTKSFNRGEC SEQ ID NO: 33: CAN03 Heavy chain constant region, Ig gamma-1 chain C region (Homo sapiens) (UnitProt Accession No. P01857)
ASTKGPSVFPLAPSSKSTSGGTAALGCLVKDYFPEPVTVSWNSGALTSGVHTFPAVLQ
SSGLYSLSSVVTVPSSSLGTQTYICNVNHKPSNTKVDKKVEPKSCDKTHTCPPCPAPEL
LGGPSVFLFPPKPKDTLMISRTPEVTCVVVDVSHEDPEVKFNWYVDGVEVHNAKTKPR
EEQYNSTYRVVSVLTVLHQDWLNGKEYKCKVSNKALPAPIEKTISKAKGQPREPQVYTL
PPSREEMTKNQVSLTCLVKGFYPSDIAVEWESNGQPENNYKTTPPVLDSDGSFFLYSK
LTVDKSRWQQGNVFSCSVMHEALHNHYT SEQ ID NO: 34: CAN03 Light chain constant region, Ig kappa chain C region (Homo sapiens) (UnitProt Accession No. P01834)
TVAAPSVFIFPPSDEQLKSGTASVVCLLNNFYPREAKVQWKVDNALQSGN
SQESVTEQDSKDSTYSLSSTLTLSKADYEKHKVYACEVTHQGLSSPVTKSFNRGEC SEQ ID NO: 35: >hu3F8-HC-hIgG1-K409R
QVQLVQSGAEVKKPGSSVKVSCKASGYAFTSSWMNWVRQAPGQGLEWMGRIYPGD
GNTHYAQKFQGRVTLTADKSTSTAYMELSSLRSEDTAVYYCGEGYLDPMDYWGQGTL
VTVSSASTKGPSVFPLAPSSKSTSGGTAALGCLVKDYFPEPVTVSWNSGALTSGVHTF
PAVLQSSGLYSLSSVVTVPSSSLGTQTYICNVNHKPSNTKVDKKVEPKSCDKTHTCPPC
PAPELLGGPSVFLFPPKPKDTLMISRTPEVTCVVVDVSHEDPEVKFNWYVDGVEVHNA
KTKPREEQYNSTYRVVSVLTVLHQDWLNGKEYKCKVSNKALPAPIEKTISKAKGQPREP
QVYTLPPSREEMTKNQVSLTCLVKGFYPSDIAVEWESNGQPENNYKTTPPVLDSDGSF
FLYSRLTVDKSRWQQGNVFSCSVMHEALHNHYTQKSLSLSPGK SEQ ID NO: 36: >hu3F8-LC-hk
DIQMTQSPSSLSASVGDRVTITCQASQGINNYLNWYQQKPGKAPKLLIHYTSGLHAGVP
SRFSGSGSGTDYTLTISSLEPEDVATYYCQQYSILPWTFGGGTKVEIKRTVAAPSVFIFP
PSDEQLKSGTASVVCLLNNFYPREAKVQWKVDNALQSGNSQESVTEQDSKDSTYSLS
STLTLSKADYEKHKVYACEVTHQGLSSPVTKSFNRGEC SEQ ID NO: 37: >ch2C9-HC-hIgG1-F405L
DVKLVESGGGLVKPGGSLKLSCAASGFTFSIYTMSWVRQTPEKRLEWVATISIGGSYIN
YPDSVKGRFTISRDNAKNTLYLQMSSLKSEDTAIYYCSREVDGSYAMDYWGQGTSVTV
SSASTKGPSVFPLAPSSKSTSGGTAALGCLVKDYFPEPVTVSWNSGALTSGVHTFPAV
LQSSGLYSLSSVVTVPSSSLGTQTYICNVNHKPSNTKVDKKVEPKSCDKTHTCPPCPAP
ELLGGPSVFLFPPKPKDTLMISRTPEVTCVVVDVSHEDPEVKFNWYVDGVEVHNAKTK
PREEQYNSTYRVVSVLTVLHQDWLNGKEYKCKVSNKALPAPIEKTISKAKGQPREPQVY
TLPPSREEMTKNQVSLTCLVKGFYPSDIAVEWESNGQPENNYKTTPPVLDSDGSFLLY
SKLTVDKSRWQQGNVFSCSVMHEALHNHYTQKSLSLSPGK -continued

| Overview of sequences |
|---|
| SEQ ID NO: 38: >ch2C9-LC-hk<br>DILLTQSPAILSVSPGERVSFSCRASQSIGTSIHWYQRRTNGSPRLLIKSASESISGIPSRF<br>SGSGSGTDFTLSINSVESEDIADYYCQQSNSWPTTFGAGTKLELKRTVAAPSVFIFPPS<br>DEQLKSGTASVVCLLNNFYPREAKVQWKVDNALQSGNSQESVTEQDSKDSTYSLSSTL<br>TLSKADYEKHKVYACEVTHQGLSSPVTKSFNRGEC |

The invention claimed is:
1. A bi-epitopic binding agent comprising:
a first antigen-binding region, and
a second antigen-binding region,
wherein the first antigen binding region and the second antigen binding region bind to different extracellular domains of human interleukin-receptor accessory protein (IL1RAP), and wherein
a) the first antigen-binding region is comprised of the following six complementary determining regions (CDRs):

```
Light chain CDR1:
                                      (SEQ ID NO: 29)
ASQGINNYLN;

Light chain CDR2:
                                      (SEQ ID NO: 9)
YTSGLHAGV or (SEQ ID NO: 22)
YTSGLHA;

Light chain CDR3:
                                      (SEQ ID NO: 10)
QQYSILPWT or (SEQ ID NO: 23)
QYSILPWT;

Heavy chain CDR1:
                                      (SEQ ID NO: 24)
GYAFTSS;

Heavy chain CDR2:
                                      (SEQ ID NO: 12)
RIYPGDGNTHYAQKFQG or (SEQ ID NO: 25)
YPGDGN;

Heavy chain CDR3:
                                      (SEQ ID NO: 13)
GYLDPMDY;
``` and
b) the second antigen-binding region is comprised of the following six complementary determining regions (CDRs):

```
Light chain CDR1:
                                      (SEQ ID NO: 16)
RASQSIGTSIH or (SEQ ID NO: 30)
ASQSIGTSIH;

Light chain CDR2:
                                      (SEQ ID NO: 17)
SASESIS;

Light chain CDR3:
                                      (SEQ ID NO: 18)
QQSNSWPTT or (SEQ ID NO: 26)
QSNSWPTT;

Heavy chain CDR1:
                                      (SEQ ID NO: 19)
GFTFSIYTMS or (SEQ ID NO: 27)
GFTFSIY;

Heavy chain CDR2:
                                      (SEQ ID NO: 20)
TISIGGSYINYPDSVKG or (SEQ ID NO: 28)
SIGGSY;

Heavy chain CDR3:
                                      (SEQ ID NO: 21)
EVDGSYAMDY,
``` wherein the first antigen-binding region comprises an amino acid sequence comprising or consisting of the heavy chain amino acid sequence SEQ ID NO: 35 and the light chain amino acid sequence SEQ ID NO: 36, and wherein the second antigen-binding region comprises the heavy chain amino acid sequence SEQ ID NO: 37 and the light chain amino acid sequence SEQ ID NO: 38.

2. The bi-epitopic binding agent according to claim 1, wherein the bi-epitopic binding agent is a dual-variable-domain antibody, a bivalent bispecific antibody, a monovalent bispecific antibody, a 'knob-in-hole' bispecific antibody, a scFv2_Fc bispecific antibody, a DVD-Ig bispecific antibody, an IgG-Fab bispecific antibody, a FAb-IgG bispecific antibody, a DART-based bispecific antibody, or a DNL-Fab3 bispecific antibody.

3. An isolated polynucleotide encoding the bi-epitopic binding agent according to claim 1.

4. A host cell comprising (a) one or more polynucleotides which, collectively or individually, encode the bi-epitopic binding agent according to claim 1; or (b) one or more expression vectors comprising the one or more of the polynucleotides in (a).

5. A pharmaceutical composition comprising the bi-epitopic binding agent according to claim 1 and a pharmaceutically acceptable excipient.

* * * * *